United States Patent [19]
DeLuca

[11] Patent Number: 5,804,413
[45] Date of Patent: Sep. 8, 1998

[54] HERPES SIMPLEX VIRUS STRAINS FOR GENE TRANSFER

[75] Inventor: Neal A. DeLuca, Cheswick, Pa.

[73] Assignee: University of Pittsburgh of the Commonwealth System of Higher Education, Pittsburgh, Pa.

[21] Appl. No.: 651,419

[22] Filed: May 22, 1996

Related U.S. Application Data

[63] Continuation-in-part of Ser. No. 479,024, Jun. 7, 1995, which is a continuation-in-part of Ser. No. 342,795, Nov. 21, 1994, Pat. No. 5,658,724, which is a continuation of Ser. No. 922,839, Jul. 31, 1992, abandoned.

[51] Int. Cl.$^6$ ............................... C12N 5/06; C12N 7/04; C12N 15/09; C12N 15/86
[52] U.S. Cl. .................. 435/69.1; 435/172.3; 435/235.1; 435/320.1; 435/364
[58] Field of Search ............................... 435/69.1, 172.3, 435/235.1, 320.1, 325, 364

[56] References Cited

U.S. PATENT DOCUMENTS

| | | | |
|---|---|---|---|
| 5,026,635 | 6/1991 | Ferguson et al. | 435/5 |
| 5,070,010 | 12/1991 | Hsu | 435/6 |
| 5,124,263 | 6/1992 | Temin et al. | 435/349 |
| 5,672,344 | 9/1997 | Kelley et al. | 424/93.2 |
| 5,674,722 | 10/1997 | Mulligan et al. | 435/172.3 |

OTHER PUBLICATIONS

Orkin et al. (Dec. 1995) Report and recommendations of the panel to assess the NIH investment in research on gene therapy, pp. 1–41.
Glorioso et al. (1992) Herpes simplex virus–based vectors. Seminars Virol. 3:265–276.
Brakefield & DeLuca, in: *Treatment of Genetic Diseases* (Desnick, ed.), 287–319, Churchill Livingstone (1991).
Brakefield and DeLuca, *The New Biologist*, 3(3), 203–18 (1991).
Chiocca et al., *The New Biologist*, 2(8), 739–46 (1990).
DeLuca & Schafer, *Nucl. Acids Res.*, 15(11), 4491–4511 (1987).
DeLuca & Schafer, *J. Virol.*, 62, 732–43 (1988).
DeLuca et al., *J. Virol.*, 56, 558–70 (1985).
Imbalzano et al., *J. Virol.*, 565–74 (1991).
Johnson et al., *J. Virol.*, 68(10), 6347–62 (1994).
Kmetz et al., *Nucl. Acids Res.*, 16(10), 4735 (1988).
McCarthy et al., *J. Virol.*, 63, 18–27 (1989).
Paterson & Everett, *Nucl. Acids Res.*, 16(23), 11005–25 (1988).
Paterson & Everett, *Virol.*, 166, 186 (1988).
Shepard et al., *J. Virol. 63*, 3714–28 (1989).
Shepard et al., *J. Viro.*, 65, 787–95 (1991).
Shih et al., *Proc. Natl. Acad. Sci. USA*, 81, 5867–70 (1984).
Westruck et al., *J. Virol.*, 64(3), 984–91 (1990).

*Primary Examiner*—George C. Elliott
*Assistant Examiner*—Robert Schwartzman
*Attorney, Agent, or Firm*—Leydig, Voit & Mayer, Ltd.

[57] ABSTRACT

Cell lines that express complementing levels of herpes simplex virus (HSV) essential immediate early proteins ICP4 and ICP27 as well as ICP4, ICP27 and ICP0 and a method of producing the novel cell lines are disclosed. These cell lines are utilized to provide HSV strains deficient for both (a) ICP4 and ICP27; (b) ICP4, ICP27, ICP22; (c) ICP4, ICP27, ICP0; and, (d) ICP4, ICP27, ICP22 and ICP0, and their generation, and HSV strains deficient for (a) ICP4 and ICP27; (b) ICP4, ICP27, ICP22; (c) ICP4, ICP27, ICP0; and, (d) ICP4, ICP27, ICP22 and ICP0, and one or more additional genes, and their generation. Vectors are provided from these methods of using these HSV strains for gene transfer and for producing site-specific homologous recombination with cellular DNA.

47 Claims, 12 Drawing Sheets

HERPES SIMPLEX VIRUS STRAINS FOR GENE TRANSFER

This application is a continuation-in-part of U.S. application Ser. No. 08/479,024, filed Jun. 7, 1995, which is a continuation-in-part of U.S. application Ser. No. 08/342,795, filed Nov. 21, 1994, now U.S. Pat. No. 5,658,724, which is a continuation of U.S. application Ser. No. 07/922,839, filed Jul. 31, 1992, now abandoned.

The invention described herein was made in the course of work supported in part by Public Health Service Grant Nos. AI27431 and AI30612 to Neal A. DeLuca from the National Institutes of Health, National Institute of Allergies and Infectious Diseases. The U.S. Government has certain rights in the invention.

1. INTRODUCTION

This invention relates to cell lines that express complementing levels of the herpes simplex virus essential immediate early proteins ICP4 and ICP27, and their generation and use; herpes simplex virus (HSV) strains deficient for both ICP4 and ICP27 their generation and use as vectors in various applications including, but not limited to, human gene therapy.

The present invention also relates to cell lines that express complementing levels of the herpes simplex virus immediate early proteins ICP4, ICP27 and ICP0 and their generation and use; herpes simplex virus strains deficient for both ICP4, ICP27 and one or more additional genes, and their generation and use as vectors in various applications including, but not limited to, human gene therapy.

The present invention also relates to novel vectors comprising ICP4$^{(-)}$ICP27$^{(-)}$ HSV strains whose genome contains at least one exogenous gene and an appropriate promoter and novel vectors comprising ICP4$^{(-)}$ICP27$^{(-)}$ additional HSV gene(s)$^{(-)}$ HSV strains whose genome contains at least one exogenous gene and an appropriate promoter; methods of using the novel HSV strains disclosed herein as vectors; and methods of using the hereinabove cited novel recombinant herpes simplex virus strains to direct homologous recombination with cellular DNA.

2. BACKGROUND OF THE INVENTION

Herpes simplex virus (HSV) contains a double-stranded, linear DNA genome comprised of approximately 152 kbp of nucleotide sequence, which encodes 75 genes. The viral genes are transcribed by cellular RNA polymerase II and are temporally regulated, resulting in the transcription and subsequent synthesis of gene products in roughly three discernable phases. These phases, or kinetic classes of genes are referred to as the Immediate Early (IE, or $\alpha$), Early (E, or $\beta$) and Late (L, or $\gamma$) genes. Immediately following the arrival of the genome of a virus in the nucleus of a newly infected cell, the IE genes are transcribed. The efficient expression of these genes does not require prior viral protein synthesis. The products of IE genes are required to activate transcription and regulate the remainder of the viral genome.

ICP4, ICP0, ICP27 and ICP22 are immediate early gene products which show varying degrees of essentiality to HSV function. These nuclear phosphoproteins possess regulatory activities thought to prime the host cell for the efficient cascade of subsequent viral gene expression, DNA replication and the production of progeny virions.

Infected Cell Polypeptide 4 (ICP4) is a large multifunctional protein. It can act as a transcription factor that either represses or activates transcription through contacts with the general transcriptional machinery. Also known as $\alpha$4, or Vmw175, ICP4 is absolutely required for both virus infectivity and the transition from IE to later transcription. Owing to its complex, multifunctional nature and its central role in the regulation of HSV gene expression, ICP4 has been the subject of numerous genetic and biochemical studies. (DeLuca, et al., 1987, Nucleic Acids Res. 15:4491–4511; DeLuca, et al., 1988, J. Virol. 62:732–743; Paterson, et al., 1988, Virology, 166:186–196; Paterson, et al., 1988, Nucleic Acids Res. 16:11005–11025; Shepard, et al., 1989, J. Virol. 63:3714–3728; and Shepard, et al., 1991, J. Virol. 65:787–795). Aiding in these studies was the development of a system to grow herpes viruses that contain mutations which inactivate essential viral proteins. In this case, cell lines were generated by cotransformation with a plasmid DNA that encoded the neomycin resistance gene from *E. coli* under the control of SV40 early promoter and a plasmid encoding the wild-type ICP4 gene. (DeLuca, et al., 1985, J. Virol. 56:558–570 and DeLuca, et al., 1987, Nucleic Acids Res. 15:4491–4511). These stable cell lines were used to generate and propagate mutant viruses that are void of ICP4 activity. (See DeLuca, et al., 1985, J. Virol. 56:558–570; DeLuca, et al., 1988, J. Virol. 62:732–743; Imbalzano, et al. 1991, J. Virol. 65:565–574; Shepard, et al., 1989, J. Virol., 63:3714–3728, 1989; and Shepard, et al., 1991, J. Virol. 65:787–795). Since the first report of this approach to HSV genetics, numerous studies have followed utilizing this strategy.

Infected Cell Polypeptide 0 (ICP0) will activate most test promoters in transient assays (Quinlan and Knipe, 1985, Mol. Cell. Biol. 5:957–963), and has been found to elevate levels of viral gene expression and growth in tissue culture, and in the trigeminal ganglia of mice (Cai and Schaffer, 1992, J. Virol. 66:2904–2915). This viral protein also facilitates the reactivation of virus from latency in a mouse model (Leib, et al., 1989, J. Virol. 63:759–768).

Infected Cell Polypeptide 27 (ICP27) also appears to be multifunctional. Several studies have shown that it can modulate the activity of ICP4 and ICP0, as well as their modification state. ICP27 has also been shown regulate viral and cellular mRNA processing events. The combined activities of ICP27 mostly contribute to efficient DNA replication and late gene expression. However, recent studies have shown that it also significantly contributes to elevated levels of early gene expression. The contribution of ICP27 to the elevated levels of some early proteins has provided an explanation for the requirement for ICP27 for viral DNA replication.

Infected Cell Polypeptide 22 (ICP22) acts to promote efficient late gene expression in a cell type dependent manner. It has also been shown to be involved in the production of a novel modified form of RNA Pol II.

It has yet to be determined how ICP4, ICP0, ICP27 and ICP22 function together to orchestrate the regulatory cascade seen in cells infected with wild type HSV. Additionally, the effects of these proteins on host cell metabolism are also unknown.

The large subunit of HSV ribonucleotide reductase, ICP6, forms a tight $\alpha_2\beta_2$ complex with the small subunit of HSV ribonucleotide reductase. This enzyme is not essential for viral growth in dividing cells. ICP6 is best classified as an HSV early gene.

From the phenotype of viruses deleted in ICP4, it became evident that such viruses would be potentially useful for gene transfer purposes. Several studies have been published exploring the potential use of such viruses for gene transfer.

(Breakefield, et al., 1991, *Treatment of Genetic Diseases*, Churchill Livingstone, Inc.; and Chocca, et al., 1990, The New Biologist 2:739–746). One property of viruses deleted for ICP4 that makes them desirable for gene transfer is that they only express a very limited subset of HSV genes including the four other IE genes: ICP0, ICP27, ICP22 and ICP47, as well as ICP6. (DeLuca, et al., 1985, J. Virol. 56:558–570). This excludes the expression of viral genes encoding proteins that direct viral DNA synthesis, as well as the structural proteins of the virus. This is desirable from the standpoint of minimizing possible deleterious effects on host cell metabolism following gene transfer.

Despite the fact viruses deleted for ICP4 are blocked at the earliest stage of infection genetically possible subsequent to the delivery of the genome to the host cell nucleus, two phenomena have complicated the use of such viruses for effective gene transfer, or therapy. First, viruses deleted for essential genes, such as ICP4-deficient viruses, require that they are propagated on cultured cells engineered to contain and express the gene deleted from the virus. (DeLuca, N. A., 1985, J. Virol. 56:558–570). This often results in a subpopulation of viruses that are no longer deleted for that gene due to homologous recombination events between the mutant viral genome and the wild-type gene resident in the host cell genome. (DeLuca, et al., 1985. J. Virol. 56:558–570). In some cases, this is minimized by deleting from the virus HSV sequences flanking the deleted gene and excluding these sequences from the plasmid used to generate the permissive transformed cell line. Therefore, the gene resident in the transformed cell line does not have flanking nucleotide sequence homology on both sides to promote homologous recombination. This is the case for the ICP4 deletion virus-transformed cell line pair, d120—E5 cells (DeLuca, et al., 1985, J. Virol. 56:558–570 and DeLuca, et al., 1987, Nucleic Acids Res. 15:4491–4511) and the ICP27 deletion virus-transformed cell line pair, 5dl1.2–2–3 cells. (McCarthy, et al., 1989. J. Virol. 63:18–27).

Secondly, despite only expressing the four other immediate early proteins, ICP4-deficient viruses are toxic to cells in culture and presumably to the majority of cells in an animal. This is most probably due to the expression of one or more of the remaining immediate early proteins and not primarily due to components of the incoming capsid since certain defective HSV virus particles, which contain all the capsid components and none of the IE genes, are not toxic. In addition, ICP4 deficient viruses shutoff host cell protein synthesis through the activity of the UL41 virion gene product (Read, et al., 1993, J. Virol. 67:7149–7160). In contrast, UV irradiated virus (Johnson, et al., 1992, J. Virol. 66:2952–2965) and mutant viruses that are also deficient in the activation function of VP16 (Johnson, et al., 1994. J. Virol. 68:6347–6362) are significantly less toxic. Infection of cells with ICP4 mutants causes chromosomal aberrations and rapid cell death (Johnson, et al., 1992, J. Virol. 66:2952–2965; Peat and Stanley, 1986. J. Gen. Virol. 67:2273–2277). Johnson and colleagues have shown that either ICP4, ICP0, ICP27 or ICP22 can significantly reduce the transformation efficiency of cultured cells to G418 resistance (Johnson, et al., 1994, J. Virol. 68:6347–6362). Therefore, a tenable hypothesis is that the activities of IE proteins perturb host cell metabolism, reducing cell viability.

A HSV mutant virus deficient for the non-essential UL41 gene product is described by Read, et al. (1993, J. Virol. 67:7149–7160). No potential use of this UL41$^{(-)}$ HSV mutant as a eukaryotic gene transfer vehicle is suggested by the authors.

HSV ribonucleotide reductase consists of a large (ICP6) and small subunit. Goldstein and Weller (1988, J. Virol. 62:196–205) disclose (1) ribonucleotide reductase activity is not essential for HSV growth, and (2) ICP6 may be inactivated via homologous recombination with a reporter gene (lacZ). The resulting ICP6$^{(-)}$:LacZ$^{(+)}$ HSV strain expresses lacZ and is not dependent upon exogenous ribonucleotide reductase for viral growth. No potential use of this recombinant HSV strain as a gene therapy vehicle is disclosed, taught or suggested.

Therefore, despite attempts to alleviate various problems with use of known HSV mutant strains upon host cell infection, a need exists for defective herpes simplex virus strains that exhibit efficient growth in a controlled laboratory complementing system, a lower level of wild-type virus regeneration and lowered cytotoxic effects.

3. SUMMARY OF THE INVENTION

The present invention provides for novel cell lines which contain DNA encoding for the HSV proteins ICP27 and ICP4. The present invention also provides for a method of producing the novel ICP4$^{(+)}$ICP27$^{(+)}$ cell lines. The method comprises cotransfecting a piece of DNA encoding for ICP27 and a piece of DNA encoding for ICP4 into a suitable cell line and selecting cells which simultaneously harbor both ICP4 and ICP27 encoding DNA. Suitable cell lines include any cell line which will host HSV and which will form colonies. The pieces of DNA encoding ICP27 or ICP4 may be introduced into the cell using any DNA delivery system, such as, for example, retroviral vectors, liposome technology, and recombinant plasmids.

A specific embodiment of the present invention is the ICP4ICP27 complementing cell line, 26 cells, which was deposited with the American Type Culture Collection (ATCC) under the terms of the USPTO on Apr. 21, 1993 and was converted to the terms of the Budapest Treaty on Mar. 7, 1996. The 26 cells cell line was assigned ATCC accession no. CRL 11332.

The present invention also provides for novel cell lines which contain DNA encoding for the HSV proteins ICP27, ICP4 and ICP0. The present invention also provides for a method of producing the novel ICP4$^{(+)}$ICP27$^{(+)}$ICP1$^{(+)}$ cell lines. The method comprises cotransfecting a piece of DNA encoding ICP0 into a suitable cell line expressing both ICP4 and ICP27, including but not limited to the 26 cells cell line. Alternatively, the method comprises cotransfecting a piece of DNA encoding ICP27, a piece of DNA encoding for ICP4 and a piece of DNA encoding ICP0 into a suitable cell line and selecting cells which simultaneously harbor ICP4, ICP27 and ICP0 encoding DNA. As noted above for ICP4$^{(+)}$ICP27$^{(+)}$ cell lines, a suitable cell line includes any cell line which will host HSV and which will form colonies. The pieces of DNA encoding ICP27, ICP4 or ICP0 may be introduced into the cell using any DNA delivery system, such as, for example, retroviral vectors, liposome technology, and recombinant plasmids.

A specific embodiment of the present invention is the ICP4ICP27ICP0 complementing cell line, FO6, deposited with the American Type Culture Collection on Jan. 30, 1996 under the terms of the Budapest Treaty. The FO6 cells cell line was assigned ATCC accession no. CRL 12028. An ICP4ICP27ICP0 complementing cell line, including but not limited to FO6, is required for optimal isolation, characterization and propagation of ICP4$^{(-)}$ICP27$^{(-)}$ICP0$^{(-)}$ viruses of the present invention. In addition, an ICP4ICP27ICP0 complementing cell line, including but not limited to FO6, is required for optimal isolation, characterization and propagation of ICP4$^{(-)}$ICP27$^{(-)}$ICP0$^{(-)}$ICP22$^{(-)}$ viruses.

The present invention provides for a method of using the novel ICP4$^{(+)}$ICP27$^{(+)}$ cell lines to produce recombinant HSV strains deficient for both ICP4 and ICP27. The method comprises co-infecting ICP4$^{(+)}$ICP27$^{(+)}$ cells with viruses deficient in ICP4 and viruses deficient in ICP27 and assaying for recombinant ICP4$^{(-)}$ICP27$^{(-)}$ progeny virus.

The present invention provides for the novel recombinant ICP4$^{(-)}$ICP27$^{(-)}$ HSV strains discussed hereinabove. The present invention also provides a method of efficiently growing the recombinant ICP4$^{(-)}$ICP27$^{(-)}$ HSV strains with an extremely low level of wild-type regeneration. The method comprises infecting ICP4$^{(+)}$ICP27$^{(+)}$ cells with a recombinant ICP4$^{(-)}$ICP27$^{(-)}$ HSV strain and collecting the progeny virus. The inventor has obtained stock titers in excess of $10^9$ plaque forming units (PFU) per milliliter (ml). The frequency of appearance of wild-type recombinant virus in the transformed cell line is calculated at $10^{-12}$. This represents an extremely low ratio of wild-type recombinant to infectious units (PFU).

A specific embodiment of the present invention is d92, a HSV strain deleted for ICP4 and ICP27. The HSV double mutant d92 was deposited with the American Type Culture Collection (ATCC) under the terms of the USPTO on Apr. 21, 1993 and was converted to the terms of the Budapest Treaty on Mar. 7, 1996. The d92 HSV strain was assigned ATCC accession no. VR 2406.

The present invention also provides for novel vectors comprising ICP4$^{(-)}$ICP27$^{(-)}$ HSV strains whose genome contains at least one exogenous gene to be transferred to a cell under the control of the appropriate promoter sequence for purposes including, but not limited to, human gene therapy or the generation of novel cell lines.

The present invention also discloses construction of herpes virus vectors comprising a ICP4$^{(-)}$ICP27$^{(-)}$ background with mutations in additional HSV genes. A novel ICP4$^{(-)}$ICP27$^{(-)}$ HSV strain (and respective complementing cell line as disclosed in this specification) are utilized to construct additional HSV strains which further decrease expressed viral proteins and concomitant deleterious post-infection effects on host cell metabolism. An additional HSV gene may be an essential or nonessential HSV gene as well as being either an α, β or Y HSV gene.

To this end the present invention relates to novel recombinant HSV strains deleted for ICP4, ICP27 and ICP22. An ICP4$^{(-)}$ICP27$^{(-)}$ICP22$^{(-)}$ mutant of the present invention imparts minimal affect on host cell structure. In addition, viral and cellular gene expression continues for onwards of four days post-infection while cellular DNA replication and cell division is inhibited. The characteristics of an ICP4$^{(-)}$ICP27$^{(-)}$ICP22$^{(-)}$ mutant as shown in Example Section 8 suggest use of these vectors in treating various tumors. For example, this mutant can be engineered to express genes that encode cytokines to stimulate immune recognition of the tumor cells, and/or suicide genes for prodrug activation such as, the tk or cytosine deaminase. The infected tumor cells will be growth arrested but express the therapeutic gene for the potential elimination of the tumor cells that remain uninfected. The combination of this approach along with the exploitation of the ICP4$^{(-)}$ICP27$^{(-)}$ICP22$^{(-)}$ phenotype is novel.

A specific embodiment of this portion of the present invention is d95, a HSV strain deleted for ICP4, ICP27 and ICP22, deposited with the ATCC on Jan. 30, 1996 under the terms of the Budapest Treaty and assigned ATCC accession no. VR2523.

The present invention also relates to novel recombinant HSV strains deleted for ICP4, ICP27 and ICP0. An ICP4$^{(-)}$ICP27$^{(-)}$ICP0$^{(-)}$ mutant of the present invention results in significant decreases in host cell toxicity as compared to d92- and d95-infected cells. The data presented in this specification shows that an ICP4ICP27ICP0 complementing cell line, such as FO6, is required for optimal isolation, characterization and propagation of these ICP4$^{(-)}$ICP27$^{(-)}$ICP0$^{(-)}$ viruses. In addition, an ICP4ICP27ICP0 complementing cell line, including but not limited to FO6, is required for optimal isolation, characterization and propagation of ICP4$^{(-)}$ICP27$^{(-)}$ICP0$^{(-)}$ICP22$^{(-)}$ viruses.

A specific embodiment of this portion of the present invention is d97, an HSV strain deleted for ICP4, ICP27 and ICP0, deposited with the ATCC on Jan. 30, 1996 under the terms of the Budapest Treaty and assigned accession no. VR2524.

The present invention also relates to novel recombinant HSV strains deleted for ICP4, ICP27, ICP0 and ICP22. An ICP4$^{(-)}$ICP27$^{(-)}$ICP22$^{(-)}$ICP0$^{(-)}$ mutant of the present invention will also result in significant decreases in host cell toxicity as compared to d92- and d95-infected cells. An ICP4ICP27ICP0 complementing cell line, such as FO6, will be required for optimal isolation, characterization and propagation of a novel virus deficient in ICP4, ICP27, ICP22 and ICP0.

Many of the genes within the HSV genome are nonessential to virus reproduction in the ICP4ICP27 complementing cell lines. Nonessential genes are those which are nonessential for growth in the ICP4ICP27 complementing cell line.

Therefore, the present invention also provides for (1) ICP4$^{(-)}$ICP27$^{(-)}$ additional HSV gene(s)$^-$ HSV strains which are ICP4$^{(-)}$ICP27$^{(-)}$ nonessential HSV gene(s)$^-$ HSV strains; (2) ICP4$^{(-)}$ICP27$^{(-)}$ICP22$^{(-)}$ additional HSV gene(s)$^-$ HSV strains which are ICP4$^{(-)}$ICP27$^{(-)}$ICP22$^{(-)}$ nonessential HSV gene(s)$^-$ HSV strains; (3) ICP4$^{(-)}$ICP27$^{(-)}$ICP0$^{(-)}$ additional HSV gene(s)$^-$ HSV strains which are ICP4$^{(-)}$ICP27$^{(-)}$ICP0$^{(-)}$ nonessential HSV gene(s)$^-$ HSV strains; and (4) ICP4$^{(-)}$ICP27$^{(-)}$ICP0$^{(-)}$ICP22$^{(-)}$ additional HSV gene(s)$^-$ HSV strains which are ICP4$^{(-)}$ICP27$^{(-)}$ICP0$^{(-)}$ICP22$^{(-)}$ nonessential HSV gene(s)$^-$ HSV strains.

The present invention also relates to novel recombinant HSV strains deleted for ICP4, ICP27 and the nonessential HSV gene, UL41. The wild type UL41 gene encodes a 58 kD viral tegument protein involved in the virion-host shutoff (vhs) of protein synthesis. UL41 is a late HSV gene product and a component of the virus.

A specific embodiment of the present invention is d33, a HSV strain deleted for ICP4, ICP27 and the non-essential gene, UL41. The d33 genome is approximately 11 kb shorter than wild type HSV.

The present invention also relates to novel recombinant HSV strains deleted for ICP4, ICP27 and the nonessential HSV genes, UL41 and UL39. The nonessential HSV gene UL39 encodes ICP6, the large subunit of ribonucleotide reductase.

Another specific embodiment of the present invention is d94, a HSV strain deleted for ICP4, ICP27, and the non-essential HSV genes UL41 and UL39, with a DNA fragment encoding β-galactosidase inserted within the UL39 coding region. The HSV strain d94 Δ(ICP4:ICP27:UL41:UL39):β-gal expresses β-gal in Vero cells without greatly altering cell morphology as compared to uninfected Vero cells.

d33 and d94 exemplify a central theme of the present invention: UL41 and UL39, alone or in combination, serve as sites of gene inactivation and replacement with a foreign gene of interest so as to generate ICP4$^{(-)}$ICP27$^{(-)}$-based gene transfer vehicles with the improved characteristics enunciated throughout this specification.

The present invention relates to using cell lines to propagate any HSV gene therapy vector which is mutated in at least HSV genes encoding for the HSV proteins ICP4 and ICP27. Such cell lines are exemplified but in no way limited to the 26 cells and FO6 cell lines described throughout this specification. The cell lines of the present invention will be required to optimally propagate any HSV gene therapy vehicle mutated for at least HSV genes encoding for the HSV proteins ICP4 and ICP27, including but not limited to various HSV gene therapy vehicles exemplified in this specification such as d92, d95, d97, d94 and d33.

It is an object of the present invention to provide novel cell lines which contain DNA encoding for the HSV proteins ICP27 and ICP4.

It is a further object of the present invention to provide a method for producing ICP4$^{(+)}$ICP27$^{(+)}$ cell lines.

It is a further object of the present invention to provide a method of using ICP4$^{(+)}$ICP27$^{(+)}$ cell lines to produce HSV strains deficient for the genes encoding the HSV proteins ICP4 and ICP27.

It is a further object of the present invention to provide novel ICP4$^{(-)}$ICP27$^{(-)}$ HSV strains.

It is a further object of the present invention to provide novel ICP4$^{(-)}$ICP27$^{(-)}$ICP22$^{(-)}$ HSV strains.

It is a further object of the present invention to provide novel cell lines which contain DNA encoding the HSV proteins ICP27, ICP4 and ICP0.

It is a further object of the present invention to provide a method of growing ICP4$^{(-)}$ICP27$^{(-)}$ HSV strains using ICP4$^{(+)}$ICP27$^{(+)}$ cell lines.

It is a further object of the present invention to provide ICP4$^{(-)}$ICP27$^{(-)}$ additional HSV gene(s)$^-$ HSV strains.

It is a further object of the present invention to provide novel ICP4$^{(-)}$ICP27$^{(-)}$ICP0$^{(-)}$ HSV strains.

It is a further object of the present invention to provide novel ICP4$^{(-)}$ICP27$^{(-)}$ICP0$^{(-)}$ICP22$^{(-)}$ HSV strains.

It is a further object of the present invention to provide ICP4$^{(-)}$ICP27$^{(-)}$ additional HSV gene(s)$^-$ HSV strains deficient in the HSV UL41 gene.

It is a further object of the present invention to provide ICP4$^{(-)}$ICP27$^{(-)}$ additional HSV gene(s)$^-$ HSV strains deficient in the HSV UL39 gene.

It is a further object of the present invention to provide ICP4$^{(-)}$ICP27$^{(-)}$ additional HSV gene(s)$^-$ HSV strains deficient in the HSV UL41 gene and the HSV UL39 gene.

It is a further object of the present invention to provide a method of producing ICP4$^{(-)}$ICP27$^{(-)}$ additional HSV gene(s)$^-$ HSV strains using ICP4$^{(+)}$ICP27$^{(+)}$ cell lines.

It is a further object of the present invention to provide a method of growing ICP4$^{(-)}$ICP27$^{(-)}$ additional HSV gene(s)$^-$ HSV strains using ICP4$^{(+)}$ICP27$^{(+)}$ cell lines.

It is a further object of the present invention to provide novel vectors comprising ICP4$^{(-)}$ICP27$^{(-)}$ HSV strains whose genome contains at least one exogenous gene to be transferred to a cell under the control of an appropriate promoter sequence.

It is a further object of the present invention to provide novel vectors comprising ICP4$^{(-)}$ICP27$^{(-)}$ additional HSV gene(s)$^-$ HSV strains whose genome contains at least one exogenous gene to be transferred to a cell under the control of an appropriate promoter sequence.

It is a further object of the present invention to provide a method of using the novel HSV strains disclosed as vectors.

It is a further object of the present invention to provide a method of using the disclosed novel HSV strains to direct homologous recombination between cellular sequences cloned into the HSV genome and cellular DNA.

It is a further object of the present invention to provide cell lines mutated for at least HSV genes encoding proteins ICP4 and ICP27 such that these cell lines optimally propagate HSV gene therapy vectors mutated for at least HSV genes encoding for ICP4 and ICP27.

These and other objects of the invention will be more fully understood from the following description of the invention with reference to the figures incorporated herein as a part to this application.

4. BRIEF DESCRIPTION OF THE FIGURES

The file of this patent contains at least one drawing executed in color. Copies of this patent with color drawing (s) will be provided by the Patent and Trademark Office upon request and payment of the necessary fee.

Figure 5:
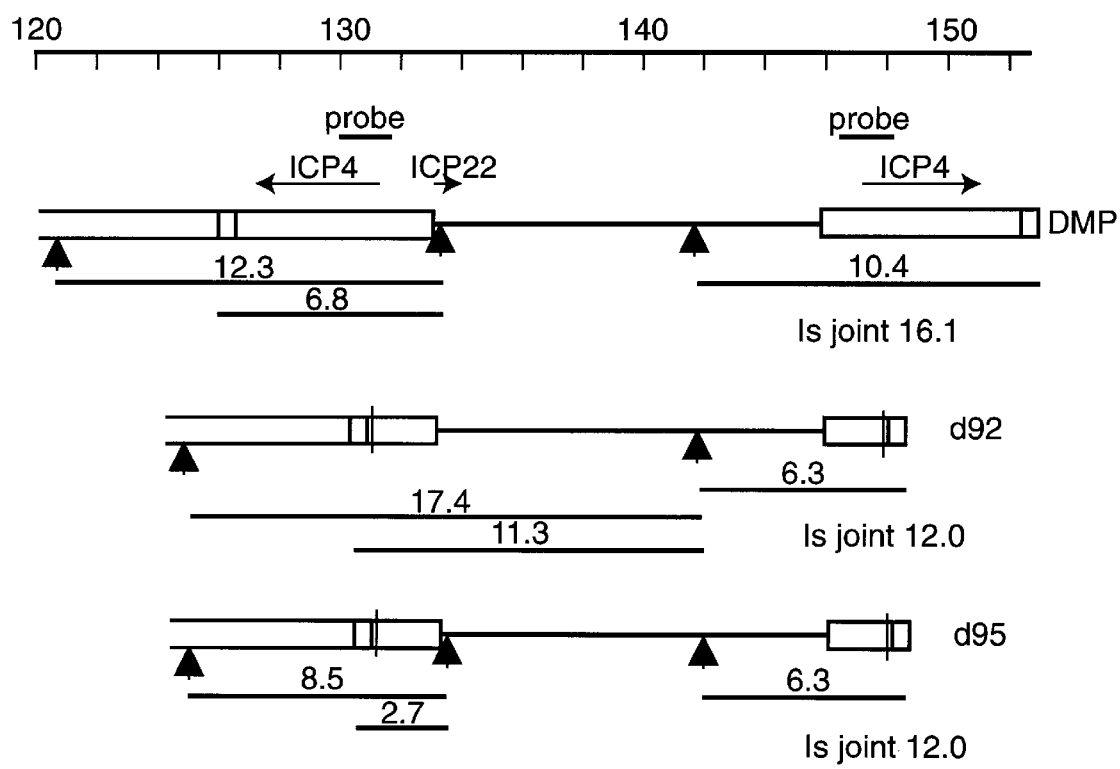

FIG. 5 shows the HSV genome from nucleotide 120 to the S terminus in the parental orientation, the locations of the genes for ICP4 and ICP22, the structures of DMP, d92, and d95 relative to the relevant HpaI restriction sites (vertical arrows). Also shown are the expected sizes of the HpaI fragments that span the ICP4 gene. The expected size of the Is joint fragment is listed for clarity.

Figure 9:
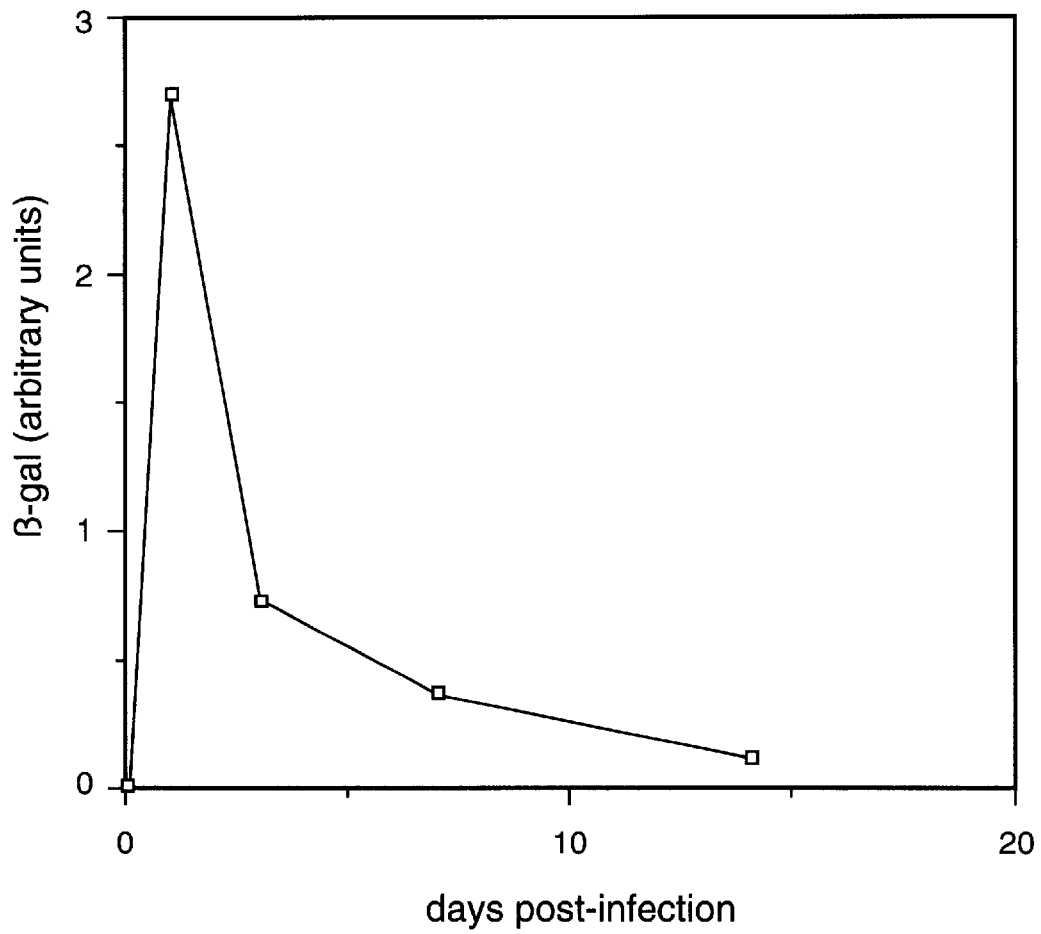

FIGS. 6A–6D shows quantitative (FIGS. 6A and 6B) and qualitative (FIGS. 6C and 6D) analysis of cellular β-tubulin RNA species identified in FIG. 9.

FIGS. 7A–7D shows inhibition of cell division and DNA replication in d95-infected cells.

Figure 7A:
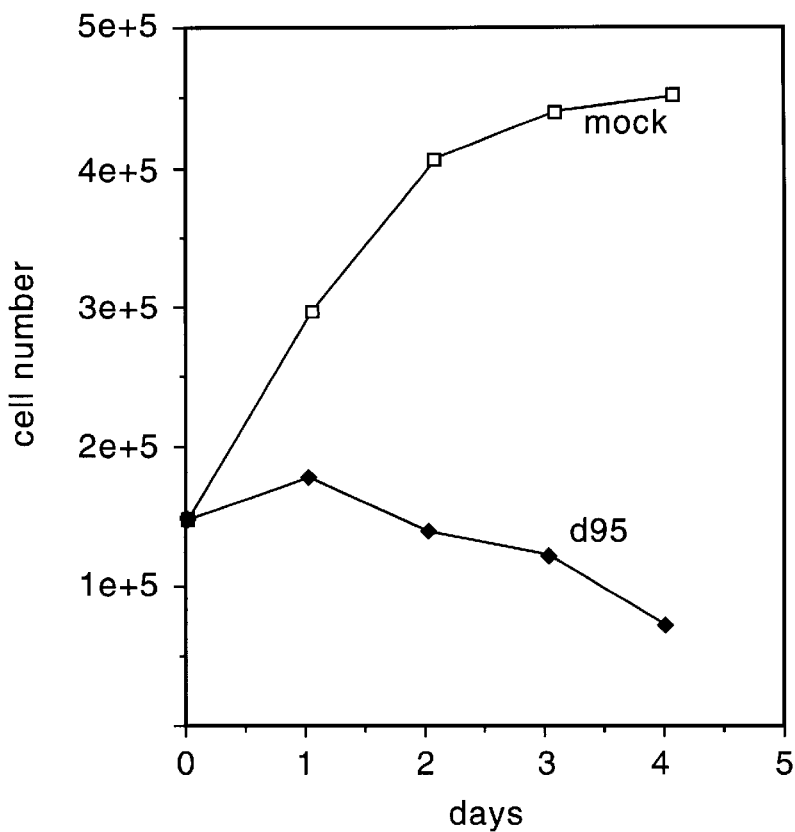

FIG. 7A shows cell number of d95-infected Vero cells at 1, 2, 3 and 4 days post infection.

Figure 7B:
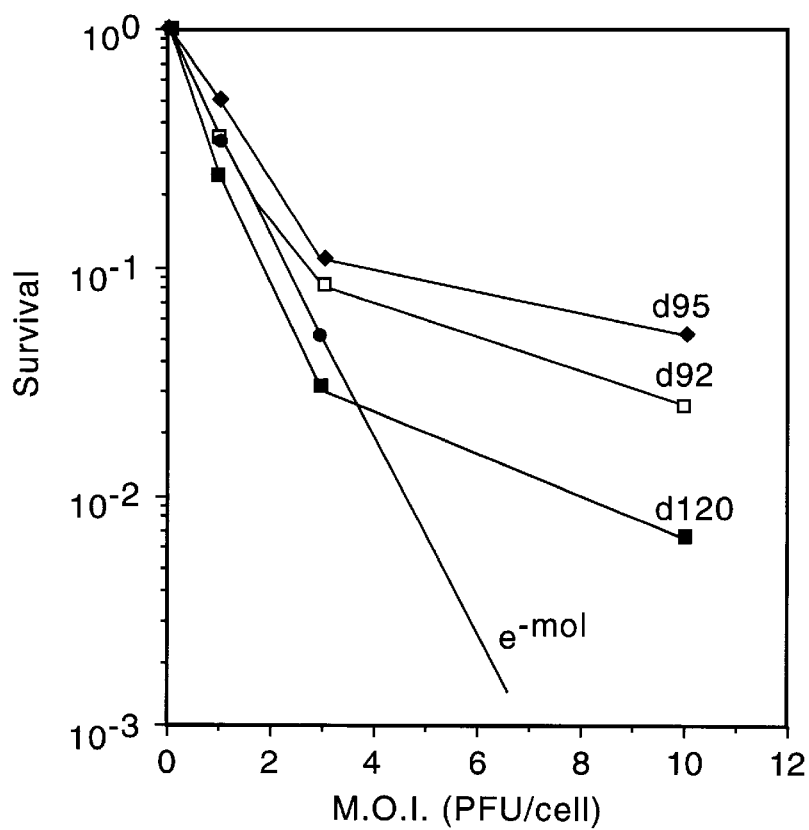

FIG. 7B shows cell survival as a function of m.o.i. of d120-infected, d92-infected, d95-infected Vero cells, and mock infected Vero cells.

Figure 7C:
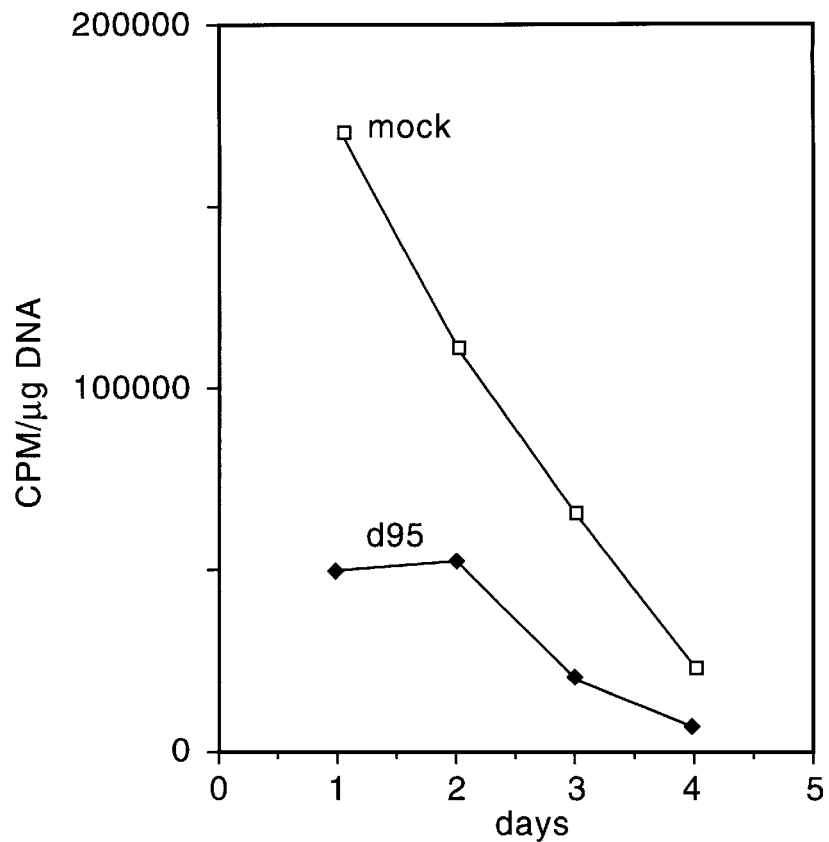

FIG. 7C shows the effect of d95 infection on host Vero cell DNA replication.

Figure 7D:
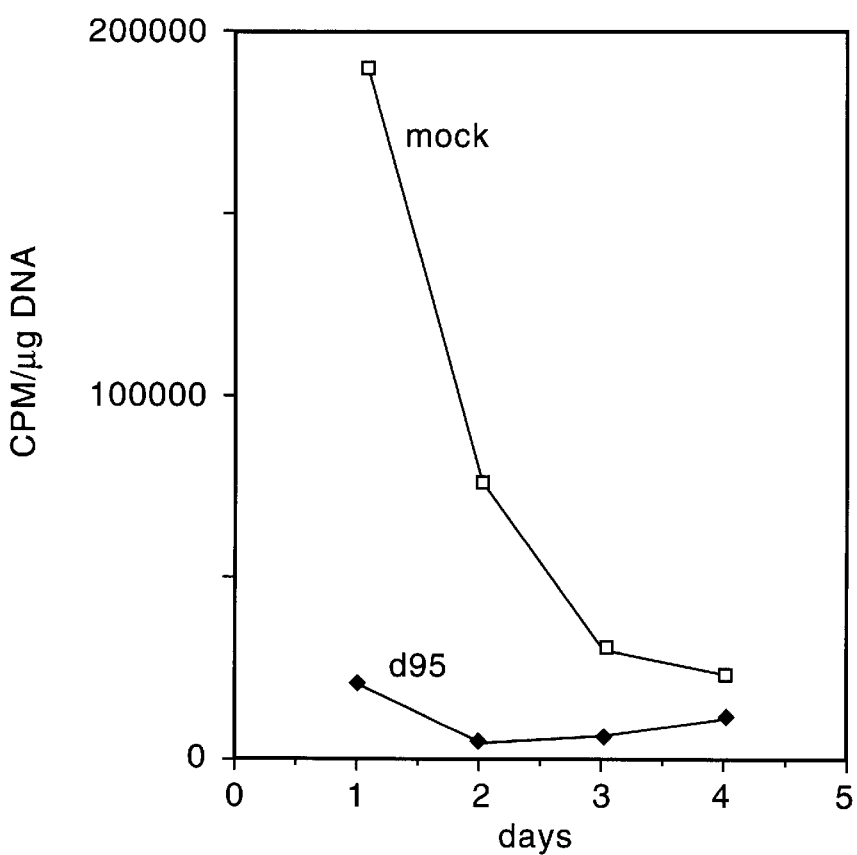

FIG. 7D shows the effect of d95 infection on host HEL cell DNA replication.

Figure 8:
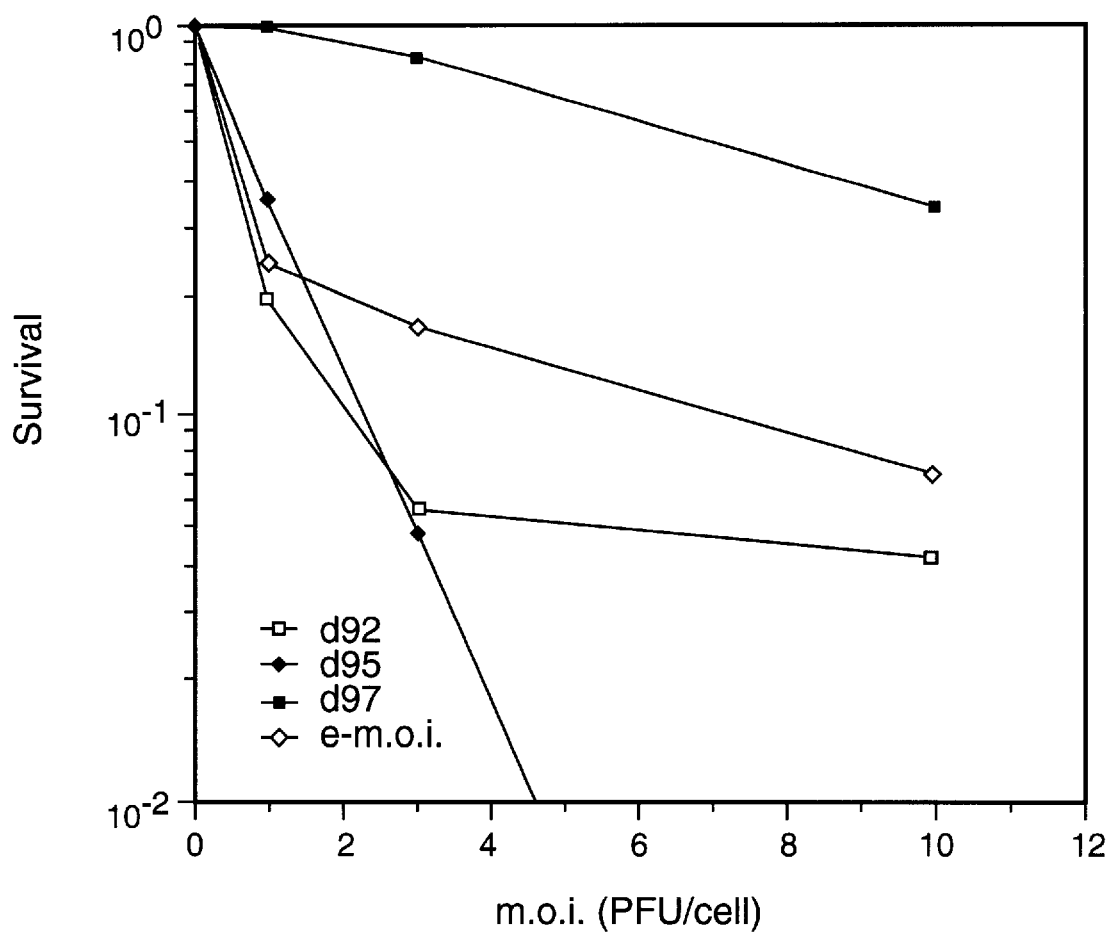

FIG. 8 shows survival of d97-, d95- and d92-infected Vero cells at mois of 1, 3, and 10. At 6 h post infection the cells were trypsinized and plated for surviving colonies.

FIG. 9 shows β-gal activity of d97-infected Vero cells over a 14 day period.

Figure 10:
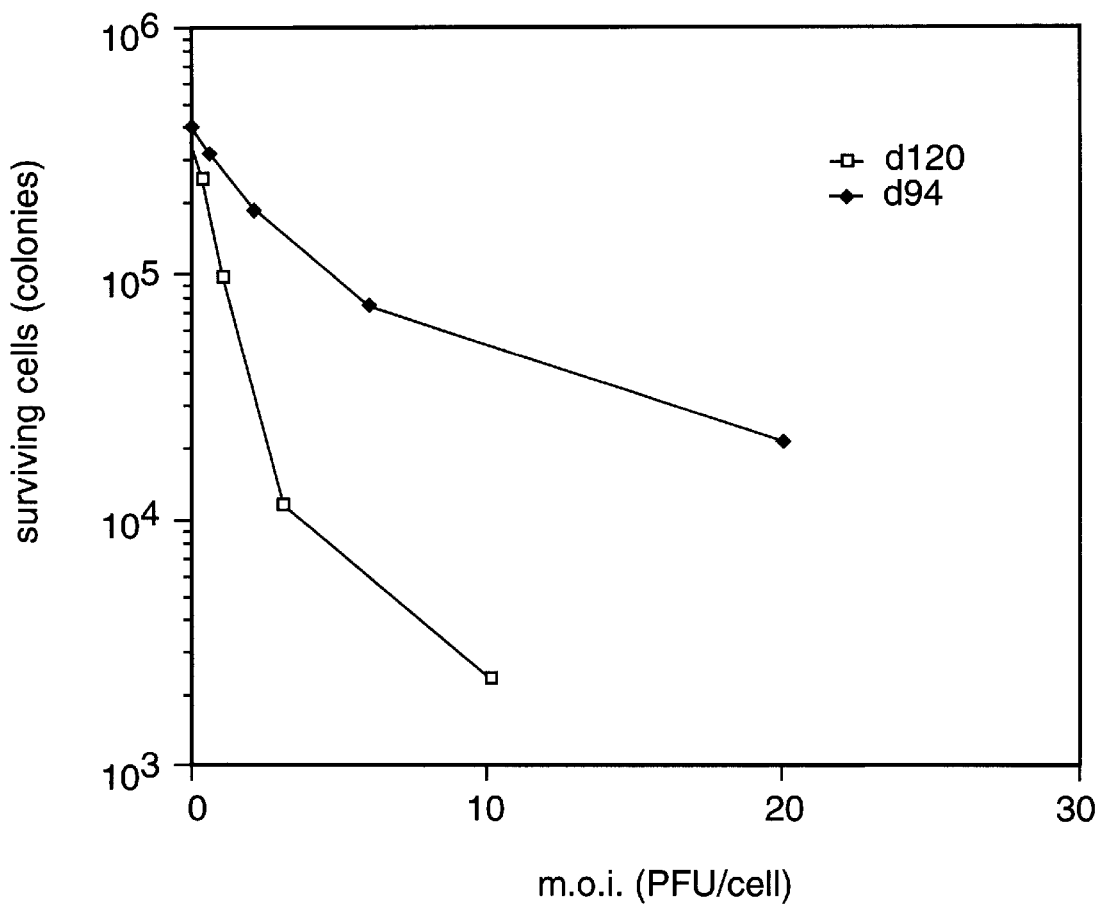

FIG. 10 shows measurements of potential cytotoxicity in d94. Survival of colony forming ability of Vero cells is plotted as a function of input multiplicity.

5. DETAILED DESCRIPTION OF THE INVENTION

As used herein, "herpes simplex virus" (HSV) means both type 1 HSV and type 2 HSV.

As used herein, "ICP4$^{(-)}$ICP27$^{(-)}$ HSV strain" means an HSV strain deficient for the HSV genes encoding ICP4 and ICP27.

As used herein, "ICP4$^{(-)}$ICP27$^{(-)}$ additional HSV gene (s)$^-$ HSV strain" means an HSV strain deficient for the HSV genes encoding ICP4, ICP27, and one or more additional HSV genes.

As used herein, "ICP4$^{(-)}$ICP27$^{(-)}$ICP22$^{(-)}$ additional HSV gene(s)$^-$ HSV strain" means an HSV strain deficient for the HSV genes encoding ICP4, ICP27, ICP22 and one or more additional HSV genes.

As used herein, "nonessential HSV gene" means an HSV gene which is nonessential to HSV replication in an ICP4ICP27 complementing cell line.

As used herein, "ICP4$^{(-)}$ICP27$^{(-)}$ nonessential HSV gene (s)$^-$ HSV strain" means an HSV strain deficient for the HSV genes encoding ICP4, ICP27, and one or more nonessential HSV genes.

As used herein, "ICP4$^{(-)}$ICP27$^{(-)}$ additional IE gene(s)$^-$ HSV strain" means an HSV strain deficient for the genes encoding ICP4, ICP27, and one or more additional immediate early HSV genes.

As used herein, "nonessential region" means a region of a genome of an HSV strain where an exogenous gene may be inserted without interfering with virus function.

As used herein, "promoter fragment" means any regulatory region or sequence which functions to effect transcription of a particular DNA fragment from which the promoter fragment is spatially related.

5.1 ICP4$^{(-)}$ICP27$^{(-)}$ HSV STRAINS AND COMPLEMENTING CELL LINES

The present invention provides for novel cell lines containing DNA encoding both the HSV proteins ICP27 and ICP4. The present invention also provides a method of producing a cell line containing DNA encoding both the HSV proteins, ICP4 and ICP27, wherein the method comprises cotransfecting cells capable of hosting HSV with pieces of DNA encoding HSV protein ICP4, and pieces of DNA encoding HSV protein ICP27; incubating said cells; and selecting cells harboring both ICP4 and ICP27 encoding pieces of DNA.

The pieces of DNA encoding ICP27 or ICP4 may be introduced into the cell using any DNA delivery system, such as, for example, retroviral vectors, recombinant plasmids, and liposome technology. Cells harboring both ICP4 and ICP27 encoding pieces of DNA may be selected by any available method. For example, the present invention encompasses the method of cotransfecting cells capable of hosting HSV with a piece of DNA encoding the HSV protein ICP4, a piece of DNA encoding the HSV protein ICP27, and a piece of DNA encoding a selection factor; incubating the cells; and selecting cells expressing DNA encoding for the selection factor. A selection factor can be anything which will allow for the selection of a cell; such as for example, a neomycin resistance protein.

A novel ICP4ICP27 complementing cell line was produced as follows: plasmids encoding the genes for ICP27 and ICP4 (shown in FIG. 1) were cotransfected with the plasmid pSV2neo into Vero cells and selected with the antibiotic G418. G418 resistant colonies were amplified and tested for the ability to host KOS (wild-type virus), and ICP4$^{(-)}$ virus, d120, and an ICP27$^{(-)}$ virus, 5dl 1.2. All possibilities were obtained: cells that host KOS (all cell lines were able to host KOS), cells that host only d120, cells that host 5dl 1.2, and cells that host both d120 or 5dl 1.2. Curiously, cells that hosted only ICP27$^{(-)}$ virus were far fewer in number than all the other types of cells obtained. Of interest were the cell lines that hosted both d120 and 5dl 1.2. One cell line, designated 26 cells, yielded 900 PFU per cell d120 and 350 PFU per cell 5dl 1.2. Another cell line, designated 8 cells, was retained because it was the only cell line that efficiently hosted 5dl 1.2 and not d120.

Although Vero cells were used in the procedure described hereinabove, it will be appreciated that the present invention encompasses use of any cell line which will host HSV and which will form colonies.

It will be further appreciated that the present invention encompasses use of any delivery system for the pieces of DNA encoding the HSV proteins ICP4 or ICP27 and which will transfect the cell lines utilized. It is preferred that the DNA fragments used to incorporate the ICP4 and ICP27 genes into the cell lines have as few as possible non-coding base pairs on their 3' and 5' ends to limit the generation of wild-type recombinant virus.

Although the plasmid pSV2neo and the antibiotic G418 were used in the procedure described hereinabove, it will be appreciated that the present invention encompasses use of any piece of DNA encoding a selection factor and any accompanying compound or technique that allows for selection of cells hosting the selection factor. It will further be appreciated that the present invention encompasses transfecting only ICP4 and ICP27 encoding pieces of DNA and using any system which allows for selection of cells harboring the ICP4 and ICP27 encoding DNA pieces. It will further be appreciated that the present invention encompasses the use of any means of introducing ICP4$^{(+)}$, ICP27$^{(+)}$ and selection factor genes into cells including but not limited to retroviral vectors, recombinant plasmids, and liposomes.

Although HSV-1 KOS wild-type virus was used in the procedure described hereinabove, it will be appreciated that the present invention encompasses use of any wild-type HSV-1 or HSV-2 virus containing both the ICP4 and ICP27 genes.

Although d120 and 5dl 1.2 were used in the procedure described hereinabove, it will be appreciated that the present invention encompasses use of any ICP4$^{(-)}$ or ICP27$^{(-)}$ HSV strains.

The method of producing a novel ICP4$^{(+)}$ICP27$^{(+)}$ cell line disclosed hereinabove is unique in that those skilled in the art would not have thought it possible to get a significant number of cells accepting both the cotransfected pieces of DNA encoding for ICP4 and pieces of DNA encoding for ICP27 and have those cells express complementing levels of both ICP4 and ICP27. The prior art teaches that such a method would produce almost solely ICP4$^{(+)}$ or ICP27$^{(+)}$ or ICP4$^{(-)}$ICP27$^{(-)}$ cell lines. Furthermore, the prior art teaches that the toxic effects of the two ICP4$^{(+)}$ and ICP27$^{(+)}$ vectors may kill any ICP4$^{(+)}$ICP27$^{(+)}$ cell almost immediately. Despite the need for such cell lines, prior research has taught that such a method would not be efficient enough to produce a cell line hosting both ICP4$^{(+)}$ and ICP27$^{(+)}$ vectors.

Production of the novel ICP4$^{(+)}$ICP27$^{(+)}$ cell lines has allowed the inventor to provide for novel recombinant HSV strains deficient for both ICP4 and ICP27. The present invention provides a method of producing an HSV strain whose genome is deficient for the HSV genes encoding ICP4 and ICP27, wherein the method comprises co-infecting ICP4ICP27 complementing cells containing DNA encoding the HSV proteins ICP4 and ICP27 within HSV strain deleted for the ICP4 gene and an HSV strain deleted for the ICP27 gene; incubating the cells; plating virus progeny from the incubated cells on the ICP4ICP27 complementing cells, ICP27 complementing cells, ICP4 complementing cells; and ICP4$^{(-)}$ICP27$^{(-)}$ cells; picking plaques; and identifying virus that plaque on ICP4ICP27 complementing cells and do not plaque on ICP27 complementing cells, ICP4 complementing cells, or ICP4$^{(-)}$ICP27$^{(-)}$ cells.

Novel ICP4$^{(-)}$ICP27$^{(-)}$ HSV strains were produced as follows: 26 cells were co-infected with d120 and 5dl 1.2, plating the progeny on 26 cells, picking plaques, and identifying isolates that plaque on 26 cells and do not plaque on 8 cells (ICP27 complementing), E5 cells (ICP4 complementing), or Vero cells. These corresponded to 8% of the total progeny; a frequency consistent with the distance between ICP4 and ICP27. Individual plaque isolates that only grew on 26 cells were examined by Southern blot hybridization to ascertain the presence of both mutations in cis. One such isolate (d92) was chosen for further study.

A Southern blot was prepared comparing the regions of the genome encoding ICP4 and ICP27 from KOS, d120, 5dl 1.2 and d92. The probe for ICP27 was the fragment used to generate the 26 cell line. It hybridizes to the NruI fragment in wild-type virus and in d120, and to a deleted form of the NruI fragment in 5dl 1.2 and d92. The probe used for ICP4 was also the same used to generate the 26 cell line, except that the ICP4 promoter was not present in the probe. It hybridized to the ICP4 containing fragments, BamHI K, P, Y and M'. M' runs off the gel because of its small size. d120 and d92 show the characteristic deletion pattern consistent with the documented 4.1 kb deletion. The heterogeneity in the size joint Bam HI fragment is due to variation in the number of "a" sequences in individual genomes. Therefore, d92 contains the intended deletions in ICP4 and ICP27, and behaves functionally as double deletion mutant.

Although Vero cells were used in the procedure described hereinabove, it will be appreciated that the present invention encompasses use of any cell line which will host HSV and which will form colonies.

Although E5 cells and 8 cells were used in the procedure described hereinabove, it will be appreciated that the present invention encompasses the use of any ICP4 complementing cells and any ICP27 complementing cells.

Although d120 and 5dl 1.2 were used in the procedure described hereinabove, it will be appreciated that the present invention encompasses use of any ICP4$^{(-)}$ or ICP27$^{(-)}$ HSV strains.

Figure 1:
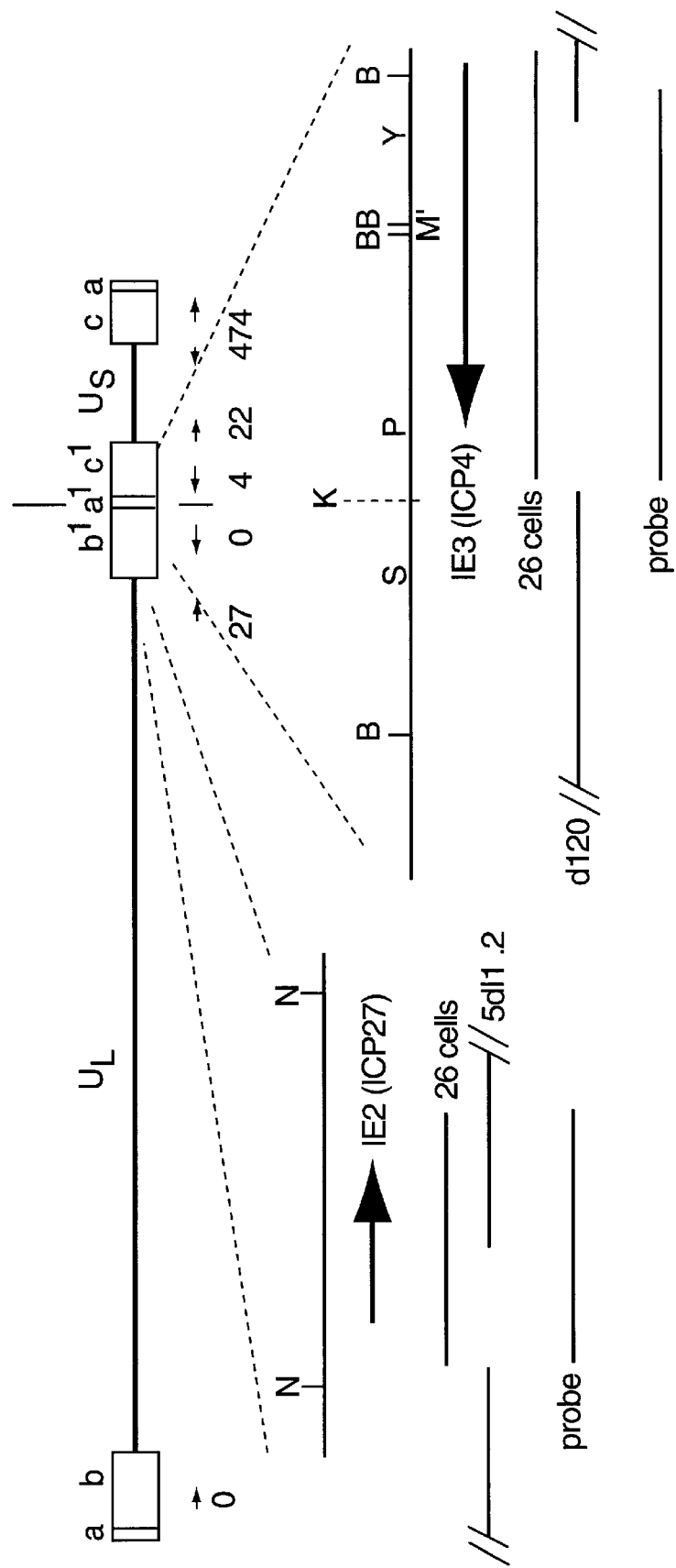
FIG. 1 shows representations of the HSV genome, the genes encoding ICP27 and ICP4, the 5dl 1.2 and d120 virus genomes with their ICP27 and ICP4 encoding fragments delineated, ICP27 and ICP4.

It is preferred that the ICP4 or ICP27 deletions in the ICP4$^{(-)}$ and ICP27$^{(-)}$ viruses be as large as possible. As shown in FIG. 1, the deletions in these viruses extend beyond the sequence of the DNA fragments used to incorporate the ICP27 and ICP4 genes in the complementing cell line. Therefore, the copies of these genes resident in the transformed cell line lack the flanking homology necessary to rescue either of the mutations in the double mutant viral genome by homologous recombination.

The present invention provides for methods of efficiently growing the novel ICP4$^{(-)}$ICP27$^{(-)}$ HSV strains disclosed herein. The method comprises infecting 26 cells with the novel ICP4$^{(-)}$ICP27$^{(-)}$ HSV strains, incubating the infected cells, and collecting the progeny virus. Due to the efficiency of these cell lines, the inventor has been able to obtain stock titers of this virus in excess of $10^9$ plaque forming units (PFU) per milliliter. This demonstrates efficient growth in the complementing cells. The prior art teaches that such growth should not be produced.

This efficiency ensures that additional genetic manipulations of the virus that have relatively mild growth damping effects may be performed, such as deletion of the remaining IE genes. The high titers obtainable in this system are also in great excess of those obtained with any of the currently used viral vector systems known to the inventor.

As far as viral vector systems are concerned, the ICP4$^{(-)}$ICP27$^{(-)}$ system described herein is considered a "helper-virus free" system. Most viral vector systems which depend upon helper virus for adequate titers of recombinant virus are notorious for the generation of wild-type, potentially pathogenic revertants. Until now, the best one has been able to do with a herpes virus system is a frequency of wild-type generation somewhat less than $10^{-6}$. Due to its construction, the ICP4$^{(-)}$ICP27$^{(-)}$ system described herein has a theoretical wild-type generation frequency less than $10^{-12}$.

The methods of producing and growing the novel recombinant ICP4$^{(-)}$ICP27$^{(-)}$ HSV strains is novel in that novel ICP4$^{(+)}$ICP27$^{(+)}$ cell lines are utilized.

A long continuous protein labelling pattern was prepared for uninfected (M), KOS, d120, 5dl 1.2- and d92-infected cells. All viruses demonstrated some some degree of shut off of host cell protein syntheses. This is probably due to the virion associated shut off gene, vhs. The only discernable viral protein present in the d92 profile is ICP6, the large subunit of ribonucleotide reductase. The absence of ICP0 in this long term label is probably due to an alteration in the stability of ICP0 as a function of the absence of ICP27. ICP0 is made to the same degree in d92 as in d120 in pulse labelling experiments. ICP27 alters the phosphorylation of a variety of proteins, including ICP0. The protein labeling pattern demonstrated that d92 does not express ICP27 or the 175 kd ICP4 protein.

In order to assess the utility of d92 and its potential derivatives as a gene transfer vector, experiments were performed to determine if and for how long d92 genomes can functionally persist in infected cells. The basis for the measurement is the ability to rescue d92 genomes via complementation with an infecting virus that has a mutation in essential gene other than ICP4 or ICP27. This method is illustrated schematically in FIG. 2.

Figure 2:
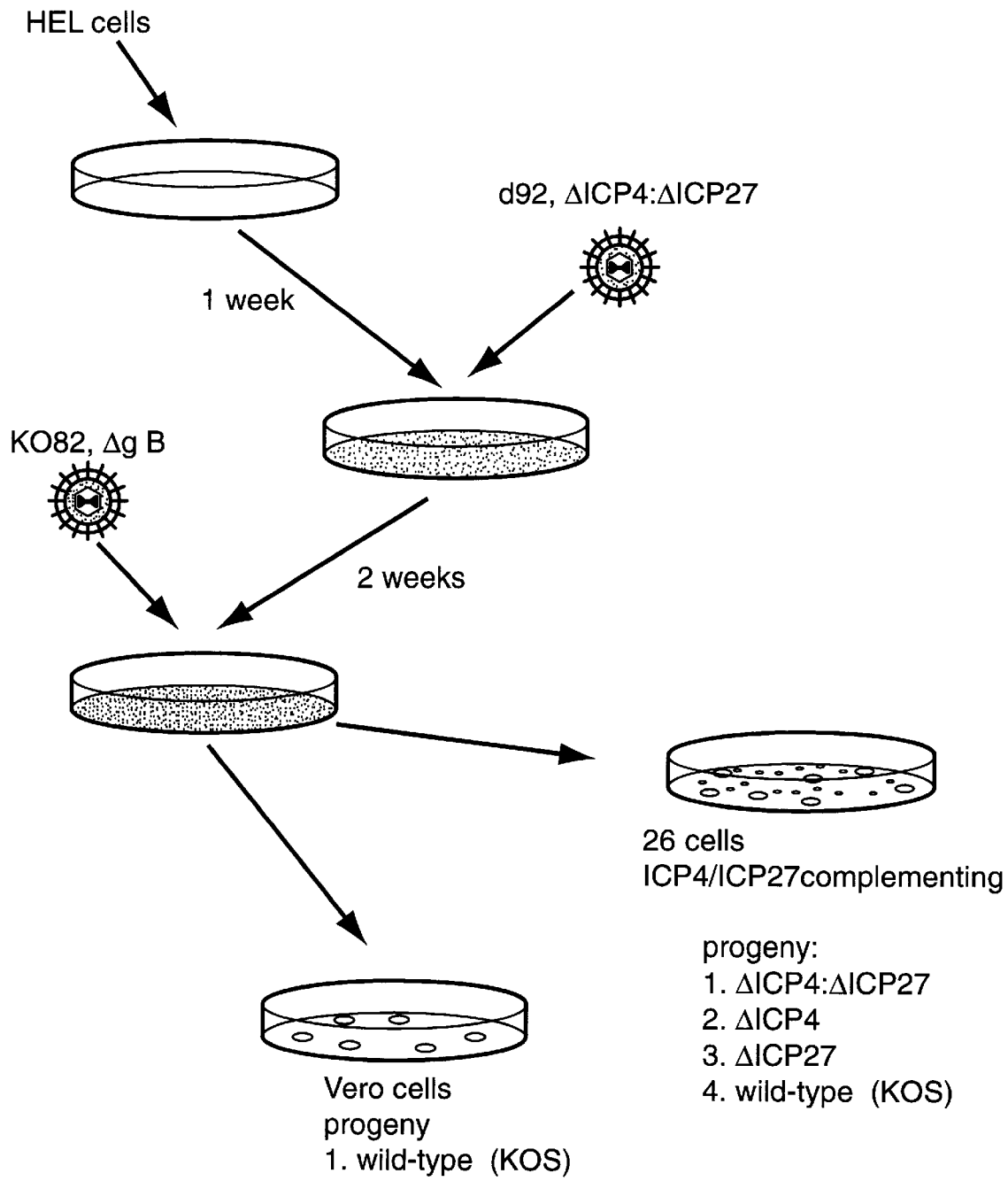
FIG. 2 shows the general method of producing d92-persistently infected HEL cells, the reactivation of virus with HSV K082 and the assay for reactivating virus on 26 cells and Vero cells.

As a direct indication of the usefulness of d92, and any of its derivatives, the following experimental approach was adopted (FIG. 2). One week old confluent normal human (primary) fibroblasts (HEL) cells were infected with d92 at a range of multiplicities of infection from 0.1 to 10 PFU/cell. At 3 and 10 PFU/cell, cytopathic effects were seen at 48 hours post-infection that were less pronounced than with d120. All the infected monolayers of HEL cells were completely restored by one week post-infection. At two weeks post-infection, the monolayers were infected with K082 (moi=3 PFU/cell), a gB deletion mutant that requires gB transformed cells for growth. 18 hours later, the monolayers were harvested for quantitation of infectious virus.

Figure 3:
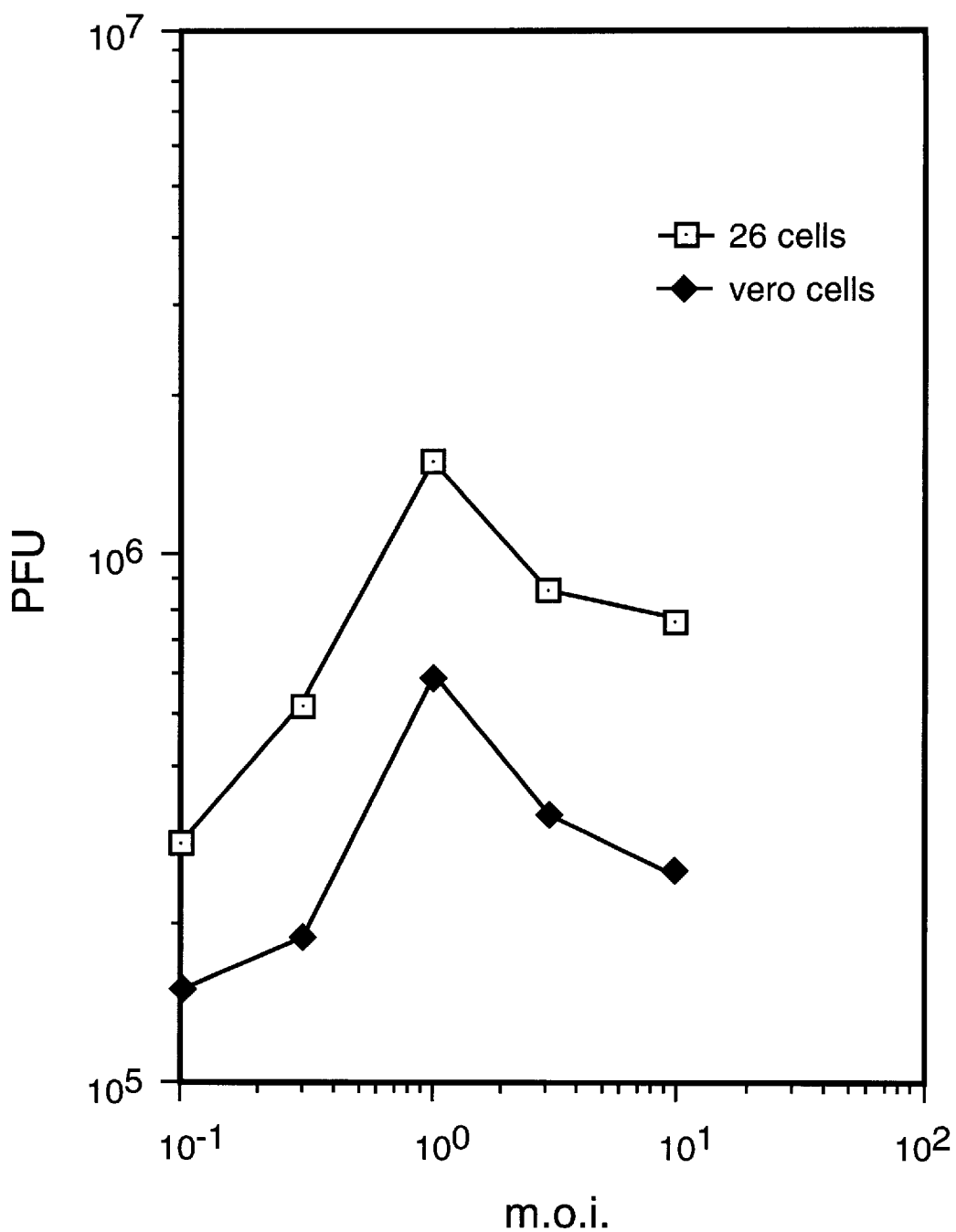
FIG. 3 is a graph of titers of progeny that can be reactivated from human embryonic lung (HEL) cells persistently infected with d92, which plate on 26 cells and on Vero cells as a function of initial input of d92. 26 cells are an ICP4$^+$ICP27$^+$cell line.

Shown in FIG. 3 are the titers of progeny that plate on 26 cells and on Vero cells as a function of initial input of d92. Three important observations can be made from the data shown in FIG. 3: (1) Substantial amounts of virus could be obtained from the week old infected cultures at all the multiplicities tested. No virus was obtained from cells infected with d92 at any of the multiplicities if the cells were not infected with K082; (2) The yield of the progeny on 26 cells was three fold higher and the plaques were smaller than that on Vero cells. Southern blots on progeny picked off of 26 cells demonstrated the presence of the deletions in ICP4 and ICP27 in the rescued virus population; and (3) The yield of virus increased linearly up to 1 PFU/cell after which the yield decreased.

From these results it is clear that a substantial number of functional d92 genomes persisted in the infected HEL cells at two weeks post-infection. Moreover, the cells retained viability sufficient to support HSV infection. The appearance of progeny on Vero cells is due to recombination between the persistent d92 genomes and the infecting K082 genomes. This is to be expected given the genomic distance between gB and ICP27. The decline in virus yield for moi's of d92 greater than 1 most probably reflects the residual cytotoxicity of d92.

Figure 4:
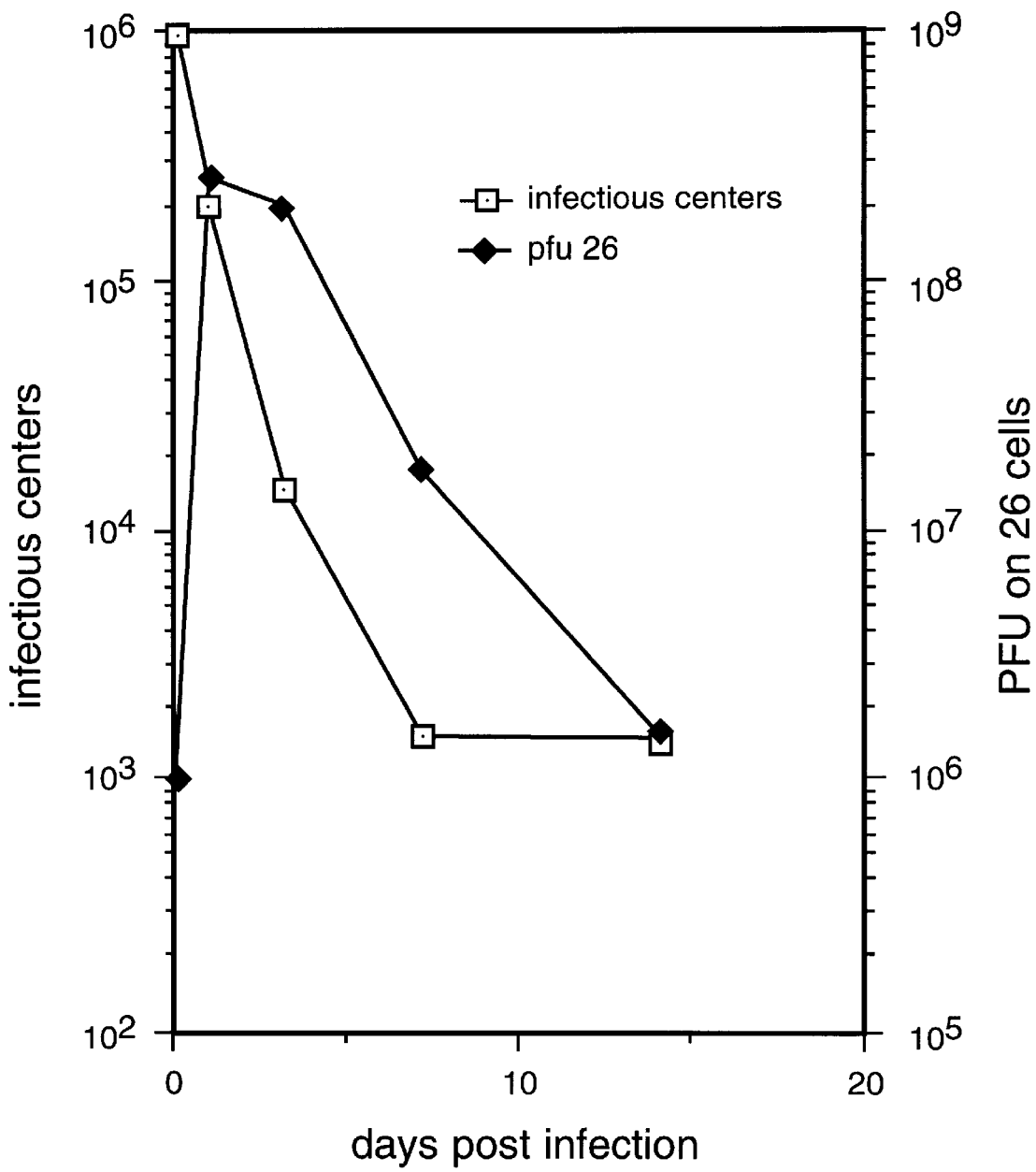
FIG. 4 is a graph of infectious centers and virus yield resulting from reactivation of d92-persistently infected HEL cells measured on 26 cells, as a function of time post-infection.

In the experiment discussed hereinabove it was established that the greatest number of functional d92 genomes persist in the HEL cells when an moi of 1 PFU/cell was used. The following experiment was performed in order to determine the number of functional persistent genomes as a function of time post-infection. Cultures of $10^6$ one week old HEL cells were infected with d92 at an moi of 1 PFU/cell. At 1, 3, 7 and 14 days post-infection the cultures were infected with K082 at an moi of 3 and incubated for 5 hours for infectious centers, or 18 hours for total virus yield. For infectious centers, the monolayers were trypsinized, diluted and plated on 26 and Vero cells. For total virus yield, the monolayers were scraped into the medium, freeze-thawed, and sonnified. The suspension was then clarified by centrifugation, diluted and plated on 26 and Vero cells. As before, the number of plaques on 26 cells was always about 2 to 4 times the number of Vero cells. Shown in FIG. 4 are the infectious centers and virus yield measured on 26 cells, as a function of time post-infection. The infectious center assay was problematic in that it was not possible to obtain single cell suspensions. If the infectious center assay were accurate, then the burst size of d92 at 3 and 7 days would be $10^4$. Wild-type HSV under optimum conditions is $10^3$.

From the burst experiment, an estimate that there are at least $10^4$ functional genomes (to give $2\times10^6$ rescued progeny) persisting at two weeks post-infection is obtained. It is not known whether there are more intact genomes in the cells that are not rescued, or whether parts of the 150 kb genome are also present in some cells.

The deletion of ICP4 and ICP27 allow for the deletion or inactivation of the remainder of the IE genes, generating a viral genome that is transcriptionally silent in the absence of exogenously added ICP4 or ICP27. The generation of a viral genome that will enter the nucleus and not express any of its encoded genes will eliminate the cytotoxic effects associated with the expression of IE proteins. This will allow for the expression of a foreign gene (under the appropriate promoter control) from the efficiently delivered HSV genome without cytotoxic side effects. This is desirable from the standpoint of safe and efficient gene therapy schemes.

The present invention provides methods of generating ICP4$^{(-)}$ICP27$^{(-)}$ nonessential HSV gene(s)$^-$ HSV strains. One method comprises co-infection of the ICP4ICP27 complementing cell line with the ICP4$^{(-)}$ICP27$^{(-)}$ HSV strain and an HSV strain harboring a deletion in the desired nonessential gene. At some frequency homologous recombination will generate a ICP4$^{(-)}$ICP27$^{(-)}$ nonessential gene(s)$^-$ recombinant virus. The progeny of this co-infection is then plated on ICP4ICP27 complementing cells and ICP4$^{(-)}$ICP27$^{(-)}$ nonessential gene(s)$^-$ HSV strains are selected. Since there is no genetic selection for the ICP4$^{(-)}$ICP27$^{(-)}$ nonessential gene$^-$ virus, Southern blot analysis of individual progeny isolates may be utilized to select ICP4$^{(-)}$ICP27$^{(-)}$ nonessential gene(s)$^-$ HSV strain. The method may be performed again to produce further nonessential gene deletions using the new ICP4$^{(-)}$ICP27$^{(-)}$ nonessential gene(s)$^-$ HSV strain and an HSV strain harboring a deletion in another desired nonessential gene. The method is repeated further as needed to provide an HSV strain having all the desired nonessential gene deletions.

A second method comprises cotransfection of the ICP4ICP27 complementing cell line with the viral DNA of the ICP4$^{(-)}$ICP27$^{(-)}$ HSV strain and pieces of DNA encoding for an inactivating mutation of the desired nonessential HSV gene. The pieces of DNA encoding the inactivating mutation of the desired nonessential HSV gene may be contained within, for example, a plasmid, vector, HSV strain or other delivery vehicle. At some frequency homologous recombination will generate a ICP4$^{(-)}$ICP27$^{(-)}$ nonessential gene(s)$^-$ recombinant virus. The progeny of this cotransfection is then plated on ICP4ICP27 complementing cells and ICP4$^{(-)}$ICP27$^{(-)}$ nonessential gene(s)$^-$ HSV strains are selected. Since there is no genetic selection for the ICP4$^{(-)}$ICP27$^{(-)}$ nonessential gene(s)$^-$ virus, Southern blot analysis of individual progeny isolates may be utilized to select ICP4$^{(-)}$ICP27$^{(-)}$ nonessential gene(s)$^-$ HSV strain. The method may be performed again to produce further nonessential gene inactivations using the new ICP4$^{(-)}$ICP27$^{(-)}$ nonessential gene(s)$^-$ HSV strain and pieces of DNA encoding an activating mutation of a further nonessential HSV gene. The method is repeated further as needed to provide an HSV strain having all the desired gene inactivations.

It will be appreciated that the methods of generating ICP4$^{(-)}$ICP27$^{(-)}$ nonessential HSV gene(s)$^-$ HSV strains disclosed hereinabove may be used together.

It will be appreciated that the present invention encompasses any method to generate ICP4$^{(-)}$ICP27$^{(-)}$ nonessential gene(s)$^-$ HSV strains which uses an ICP4ICP27 complementing cell line. As discussed throughout this specification, ICP4 and ICP27 are the only immediate early proteins absolutely essential for virus growth. The basis for the construction of the nontoxic HSV vectors is provided within this specification by the derivation of a system to propagate HSV strains deleted for ICP4 and ICP27. Construction of ICP4$^{(-)}$ICP27$^{(-)}$ HSV strains as discussed in this specification render possible the deletion of additional HSV genes, resulting in ICP4$^{(-)}$ICP27$^{(-)}$-based HSV strains with a concomitant decrease in host cell toxicity.

The present invention discloses that infection of an ICP4$^{(-)}$ICP27$^{(-)}$ HSV mutant in a eukaryotic cell, as exemplified by d92 infection of Vero cells, results in (1) ICP6 being abundantly expressed post-infection, and (2) that some degree of shut off of host protein synthesis occurs post-infection.

As stated hereinbefore, the herpes virus has many properties which would be potentially useful for gene transfer purposes. The present invention provides novel vectors comprising a novel HSV strain disclosed herein and at least one exogenous gene to be transferred to a cell and appropriate promoter sequences, wherein the gene to be transferred to a cell and the corresponding promoter sequence are contained within one or more nonessential regions of the genome of the novel HSV strains. The nonessential regions of HSV genome are well known to those skilled in the art. The present invention also provides a method of using ICP4$^{(-)}$ICP27$^{(-)}$ HSV strains as vectors, wherein the method comprises inserting at least one exogenous gene and appropriate promoter sequence into the genomes of the ICP4$^{(-)}$ ICP27$^{(-)}$ HSV strains, and then infecting cells with the ICP4$^{(-)}$ICP27$^{(-)}$ HSV strain. The present invention also provides a method of using ICP4$^{(-)}$ICP27$^{(-)}$ additional HSV gene(s)$^-$ HSV strains as vectors, wherein the method comprises inserting at least one exogenous gene and appropriate promoter sequence into the genomes of the ICP4$^{(-)}$ICP27$^{(-)}$ additional HSV gene(s)$^-$ HSV strain, and then infecting a cell with the ICP4$^{(-)}$ICP27$^{(-)}$ HSV gene(s)$^-$ HSV strain.

The inventor has demonstrated that $10^4$ to $10^5$ functional d92 viral genomes persist in $10^6$ HEL cells at one to two weeks post-infection. This gives a lower limit on the amount of vector-delivered DNA persisting in the cells at these times. This efficiency is bound to increase with further HSV gene deletions, which reduce the cytotoxicity of d92. Given the occurrence of a substantial number of persisting genomes, it follows that integration events through nonhomologous recombination will occur between the persisting viral genome and the cellular DNA. Several observations support the occurrence of extremely efficient gene transfer: (1) DNA introduced into mammalian cells is often integrated in nonhomologous sites, (2) Ultraviolet (UV) inactivated HSV were the first virus vehicles used to transform tk$^{(-)}$ cells to the tk$^{(+)}$ phenotype. UV irradiated virus were able to transform cells at low frequencies. For this purpose, high doses of UV are required to inactivate virus stocks to a level such that residual infectivity is not a problem. Under these circumstances, the transforming DNA is certain to have incurred significant UV damage; an undesirable property when one wishes to introduce biologically active genetic information. The use of nonirradiated, noncytotoxic vectors would obviate this problem; and (3) This has recently been accomplished for ICP4$^{(-)}$ virus transforming cells with the neomycin resistance gene.

While the ICP4$^{(-)}$ viruses have been shown capable of introducing transforming DNA into cultured cells, several observations suggest that d92 and additional HSV gene deficient viruses will be more efficient: (a) The level of recombinants in the ICP4$^{(-)}$ICP27$^{(-)}$ system are far lower than the lowest obtainable in the ICP4$^{(-)}$ system. This will allow us to routinely use higher moi's without the fear of the presence of chance wild-type recombinant; (b) More persistent genomes are obtainable with d92 than ICP4$^{(-)}$ viruses; and (c) Further mutational alterations made on d92 that reduce its cytotoxicity will also increase its transformation efficiency.

The present invention provides that vectors may be produced from the novel HSV strains disclosed herein by any known techniques, including, but not limited to, classical genetic or recombinant techniques. In addition, the novel vectors may be utilized by known methods. For example, a vector for neomycin resistance may be produced and utilized. The gene encoding the bacterial protein neomycin phosphotransferase is contained on the plasmid pSV2neo under the control of the SV40 promoter. The entire gene with the promoter will be placed in the Sac 1 site within the cloned HSV tk gene. The resulting plasmid will be cotransfected with recipient intact viral DNA on complementing 26 cells. The progeny of the transfection will be plated on 26 cells in the presence of acycloguanosine ($1\times10^4$M) for the selection of the tk$^{(-)}$ phenotype. Southern blots on small cultures from individual plaque isolates will be performed to identify the introduced neo$^r$ gene. The desired viruses will be further plaque purified and stocks will be prepared on 26 cells. Vero cells will be used as recipients for the neo$^r$ virus. The stable presence and function of the gene in transformed cells will be selected for by incubation in the drug G418.

As another example, a vector for the human HPRT gene may be produced and utilized. The human HPRT gene under the control of the HSV tk promoter has been cloned into the tk gene of wild-type HSV. This virus is referred to as HSV-HP40 and d92 (or its derivatives) will be co-infected on 26 cells in a classical cross experiment. Progeny that grow in the presence of acycloguanosine (tk interrupted by HPRT) on 26 cells, but not on Vero cells (containing the mutations in ICP4 and ICP27) will be isolated and the genomes examined by Southern blot hybridization to confirm the presence of all the alleles. The distance between ICP27 and tk is great enough to allow 20%–30% recombination. B103-4C cells are a HPRT derivative of B103 rat neuroma cells. Infected B103-4C cells will be incubated in HAT medium to select for HPRT$^+$ transformants. HAT medium contains 110 $\mu$M hypoxanthine, 2.3 $\mu$M aminopterin, and 20 $\mu$M thymidine. The same mechanical procedures will be used for the cloning and DNA analysis of B103-4C cells as were used for Vero cells above.

It will be appreciated that the present invention encompasses use of the novel HSV strains disclosed herein as vectors carrying any genes whose size permits them to be inserted in the HSV genome. It will be further appreciated that the novel vectors disclosed herein may be utilized for gene therapy and other known vector uses.

The unique properties of the herpes virus allow the novel HSV strains disclosed in the present invention to be used for mutational inactivation of normal cellular genes or for the repair of mutant cellular genes, by homologous recombination. The present invention provides a method of directing homologous, site-specific recombination in cellular DNA, wherein the method comprises infecting a cell with a large quantity of a vector, wherein the vector comprises: (1) an HSV strain whose genome is deficient for the HSV genes encoding the proteins ICP4 and ICP27 or the proteins ICP4, ICP27, and one or more additional HSV genes, and (2) a gene to be transferred contained within one or more nonessential regions of the HSV genome, the gene to be transferred being homologous to a gene existing within the cell.

The creation of sequence specific alterations in DNA has long been the goal of genetic research. It allows for the precise elimination and repair of biological function. In simple systems, this often involves the routine practice of generating genetic recombinants through the crossover of DNA sequences that share sequence identity. From the standpoint of altering the genome of the mammalian cell in a defined way, the generation of site-specific recombinants has been possible but occurs at a very low frequency. It has long been known that DNA introduced into mammalian cells is integrated into nonhomologous sites. Given that homologous recombination between specific sequences in the chromosome and introduced DNA occurs at a very low frequency, it follows that a nontoxic method to introduce numerous copies of homologous DNA into all the cells in a given culture would be desirable for this purpose. In addition, if the homologous DNA is vectored into the target cells by a genome that has evolved a mechanism to persist in those cells, this adds to the probability that homologous events will occur. The novel herpes virus vectors of the present invention uniquely meet these criteria. In addition, the large capacity of HSV for exogenous DNA is desirable from the standpoint of transducing genomic copies of cellular genes.

An example of a method of directing site-specific homologous recombination would be the homologous knock-out of the HPRT gene. The SV40 neo gene will be inserted into a 10.5 kb piece of human DNA that encodes exons 4 and 5 of human HPRT, such that exon 4 is deleted. This piece of DNA is contained on an Eco R1 fragment. This entire cassette will be inserted at the 3' end of the HSV tk gene. The tk gene contains a mutation that confers temperature sensitivity and is under the control of the stronger ICP4 promoter instead of the tk promoter. The HSV sequences that flank the tk gene in the proposed genome flank the construct. The constructed plasmid will be cotransfected with the appropriate intact HSV vector DNA onto 26 cells. The progeny of the transfection will be plated at 39.6° C. in the presence of acycloguanosine (100 $\mu$M) for the selection of tk$^-$ virus. Homologous recombination, introducing the ts tk into the genome will result in a tk$^{(-)}$ phenotype at the elevated temperature. Plaques isolated at 39.6° C. will be amplified and analyzed by Southern blot for the presence of the HPRT and neo DNA linked to the ts tk gene.

The HPRT:neo transducing virus will be used to infect human HepG2 cells. HepG2 cells are a hepatocellular carcinoma cell line derived from a human male. G418 will select for stable integration events, as above. These events can be either nonspecific or homologous. Gancyclovir ($2\times10^{-6}$M) selection will be simultaneously applied to select against the integration of tk along with the neo gene. This procedure has been previously shown to enrich for homologous recombination events which naturally should exclude the tk gene. In addition, 6-thioguanine (14 $\mu$g/ml) selection will also be applied to select for inactivation of the HPRT protein by the interruption of part of the gene. Isolated colonies will be analyzed by Southern blots to ascertain whether the homologous event occurred. The above scheme uses the tk gene within the HSV genome, the large capacity for foreign DNA in the HSV genome, and three strong selections to site-specifically inactivate the HPRT gene.

The larger the DNA sequence being transferred, and the greater the amount of virus infecting the cell, the greater the amount of homologous recombination. It will be appreciated that the present invention encompasses using the novel HSV strains disclosed herein to produce homologous recombination with any DNA segment which has a homologous cellular DNA counterpart and which may be carried by the herpes virus.

5.2 ICP4$^{(-)}$ICP27$^{(-)}$ ADDITIONAL IE GENE(S)$^-$ HSV STRAINS

So far, the production of virus (d92) that is deficient for the only two essential IE genes, ICP4 and ICP27 has been described. The expression of viral genes in the d92 background is limited to ICP6, ICP0, ICP22 and ICP47. Although the ICP0 protein is expressed from the d92 genome, its stability may be reduced due to the absence of ICP27 gene product (see FIG. 2). As previously stated, an important feature of this system is that the flanking homologies necessary to rescue the deletions in the virus (d92) are not present with the genes resident in the complementing cell line (26 cells). Therefore, the generation of wild-type recombinants is an extremely improbable event, and in practice they are not seen. This is extremely important not only from the standpoints of the development of "safe" vectors but also for the ability to delete other viral genes (such as for example ICP0) that may have a growth dampening effect.

The present invention provides novel HSV strains deficient for ICP4, ICP27, and one or more additional HSV genes, including HSV strains deficient for all IE genes. Viral gene expression in some of these HSV strains will be more limited than previously observed. The generation of a viral genome that will enter the nucleus and not express any of its encoded genes will eliminate the cytotoxic effects associated with the expression of IE proteins. This will allow for the expression of a foreign gene (under the appropriate promoter control) from the efficiently delivered HSV genome without cytotoxic side effects. This is desirable from the standpoint of safe and efficient gene therapy schemes.

To this end, the present invention discloses additional recombinant HSV mutant strains derived from d92 or a d92-based genome, any such HSV strain being deficient in ICP4, ICP27 and one or more essential and/or non-essential HSV gene(s).

A first additional recombinant HSV mutant strain of the present invention is an HSV strain deleted for ICP4, ICP27 and ICP0. This HSV triple mutant is exemplified, but certainly not limited to, the HSV strain d97, a HSV mutant strain deposited with the ATCC on Jan. 30, 1996 under the terms of the Budapest Treaty and assigned ATCC accession no. VR2524. An ICP4$^{(-)}$ICP27$^{(-)}$ICP0$^{(-)}$ mutant of the present invention results in significant decreases in host cell toxicity as compared to d92- and d95-infected cells.

It is disclosed by the inventor that attempts to delete ICP0 from an HSV genome deleted in ICP4 and ICP27 were problematic when the 26 cells cell line is utilized. Therefore, a novel cell line expressing complementing levels of ICP4, ICP27 and ICP0 was generated by the inventor in order to promote useful isolation, characterization and propagation of recombinant HSV strains deleted at least for ICP4, ICP27 and ICP0. One such ICP4ICP27ICP0 complementing cell line is exemplified, but certainly not limited to, the cell line FO6. This cell line was deposited with the American Type Culture Collection on Jan. 30, 1996 under the terms of the Budapest Treaty. The FO6 cells cell line was assigned ATCC accession no. CRL 12028. Therefore, an ICP4ICP27ICP0 complementing cell line, including but not limited to FO6, is required for optimal isolation, characterization, and propagation of the ICP4$^{(-)}$ICP27$^{(-)}$ICP0$^{(-)}$ viruses of the present invention. In addition, an ICP4ICP27ICP0 complementing cell line, including but not limited to FO6, is required for optimal isolation, characterization and propagation of ICP4$^{(-)}$ICP27$^{(-)}$ICP0$^{(-)}$ICP22$^{(-)}$ viruses.

A novel ICP4ICP27ICP0 complementing cell line was produced as follows: the 26 cells cell line was transformed with plasmids pW3-HS8 (Sacks and Schaffer, 1987, J. Virol. 61:829–839) and pSV2hyg. The ICP4ICP27 26 cells, which are resistant to G418, were transformed with 5 $\mu$g of pW3-HS8 and 1 $\mu$g of pSV2hyg. Colonies were selected in the presence of G418 and hygromycin. All cell lines complemented d92. Only one of the 80 colonies screened also efficiently complemented both d92 and n212, a previously published ICP0 mutant. This clone, FO6, resulted in a 30 fold increase in the number of ICP0 mutant virus plaques. The FO6 cell line was used for the isolation of a HSV virus deficient in ICP4, ICP27 and ICP0.

Although the 26 cells cell line was used in the procedure described hereinabove, it will be appreciated that the present invention encompasses use of any cell line which will host HSV and which will form colonies with complementing levels of ICP4, ICP27 and ICP0.

It will be further appreciated that the present invention encompasses use of any delivery system for the pieces of DNA encoding the HSV proteins ICP4, ICP27, ICP0 and which will transfect the cell lines utilized. It is preferred that the DNA fragments used to incorporate the ICP4, ICP27 and ICP0 genes into the cell lines have as few as possible non-coding base pairs on their 3' and 5' ends to limit the generation of wild-type recombinant virus.

Although the plasmid pSV2neo (antibiotic G418) and pSV2hyg (antibiotic hygromycin) were used in the procedure described hereinabove, it will be appreciated that the present invention encompasses use of any piece of DNA encoding a selection factor(s) and any accompanying compound or technique that allows for selection of cells hosting the selection factor(s). It will further be appreciated that the present invention encompasses transfecting only ICP4, ICP27 and ICP0 encoding pieces of DNA and using any system which allows for selection of cells harboring the ICP4, ICP27 and ICP0 encoding DNA pieces. It will further be appreciated that the present invention encompasses the use of any means of introducing ICP4$^{(+)}$, ICP27$^{(+)}$, ICP27$^{(+)}$ and selection factor genes into cells including but not limited to retroviral vectors, recombinant plasmids, and liposomes.

The data in Example Section 9 show that, as noted above, an ICP4ICP27ICP0 complementing cell line is required to optimally obtain and grow an ICP4$^{(-)}$ICP27$^{(-)}$ICP0$^{(-)}$ defective HSV mutant such as d97. The d97 HSV strain imparts minimal or no effect on host cell protein synthesis and is relatively non-toxic. Additionally, d97 will support transgene expression up to and perhaps beyond two weeks post infection.

d97 and FO6 exemplify a preferred embodiment of the present invention: a ICP4$^{(-)}$ICP27$^{(-)}$ICP0$^{(-)}$ defective HSV triple mutant which is isolated and propagated in a ICP4ICP27ICP0 complementing cell line wherein this triple mutant is capable of housing and expressing one or more transgenic sequences such that infection of a host target cell in a gene therapy application will exhibit minimal effect on target cell protein synthesis, minimal, if any, target cell toxicity and support transgene expression at least up to two weeks post infection. In other words, a ICP4$^{(-)}$ICP27$^{(-)}$ICP0$^{(-)}$ defective HSV triple mutant, as exemplified by d97 and obtained by use of FO6, exhibits the characteristics of a useful gene therapy vehicle.

Therefore, a ICP4$^{(-)}$ICP27$^{(-)}$ICP0$^{(-)}$ defective HSV triple mutant of the present invention may be utilized directly as a vector in a gene therapy application or, as described further in this section, in an additional co-infection in FO6 cells with an ICP4$^{(-)}$ICP27$^{(-)}$ICP0$^{(-)}$ defective HSV triple mutant to isolate, characterize obtain and grow a HSV quadruple mutant, including but not limited to a HSV quadruple mutant deleted for ICP4, ICP27, ICP0 and ICP22.

The identification of d97 exemplifies but in no way limits this portion of the invention. It will be within the purview of the artisan to construct a ICP4$^{(-)}$ICP27$^{(-)}$ICP0$^{(-)}$ defective HSV triple mutant by another related methodology. Mutant HSV viral strains d92 and Oβ were used in construction of d97. However, it will be appreciated that the present invention encompasses use of any ICP4$^{(-)}$, ICP27$^{(-)}$, ICP0$^{(-)}$, or a double mutant strain such as an ICP4$^{(-)}$ICP27$^{(-)}$, ICP0$^{(-)}$ICP4$^{(-)}$, or ICP0$^{(-)}$ICP27$^{(-)}$ strain to generate a ICP4$^{(-)}$ICP27$^{(-)}$ICP0$^{(-)}$ virus. This may lead to mutant strains such as d97 wherein an exogenous gene replaces a wild type gene (e.g., β-gal for ICP0) or where a large portion of the wild type gene is deleted (e.g., ICP4 and ICP27 of d92). Regardless of the related strategy, the end result will be a HSV mutant strain deleted for ICP4, ICP27 and ICP0, and hence, a HSV mutant strain which is an excellent candidate for further use as a human gene therapy vector.

A second additional recombinant HSV mutant strain of the present invention is a HSV strain deleted for ICP4, ICP27 and ICP22. This HSV triple mutant is exemplified, but certainly not limited to, the HSV strain d95, a HSV mutant strain deposited with the ATCC on Jan. 30, 1996 under the terms of the Budapest Treaty and assigned ATCC accession no. VR2523. The data presented in Example Section 8 show that a ICP4ICP27 complementing cell line such as 26 cells supports isolation, characterization and growth of a ICP4$^{(-)}$ICP27$^{(-)}$ICP22$^{(-)}$ defective HSV mutant such as d95. The d95 HSV strain imparts fewer toxic effects upon target cells in comparison to d92. Cells infected at an m.o.i of 10 with an ICP4:ICP27:ICP22 mutant such as d95 retain a relatively normal morphology, and express genes from the viral and cellular genome for three days post infection whereas viral and cellular gene expression as a function of d92 infection (m.o.i.=10) can only be analyzed for 1 day post-infection. However, when cell survival was measured by the capacity of the infected cells to form colonies, an ICP4:ICP27:ICP22 (d95) mutant inhibited colony formation similarly to cells infected with an ICP4:ICP27 (d92) mutant. The data presented in Example Section 8 show that host cell DNA synthesis was inhibited in cells infected with HSV triple mutants simultaneously deficient in ICP4:ICP27:ICP22. Additionally, d95-infected cells accumulate ICP0 in fine punctate structures within the nucleus at early times post infection, and these structures coalesce or grow to large circular, or spherical shaped objects visible by phase contrast microscopy. Therefore, while abundant accumulation of ICP0 in the absence of ICP4, ICP22, and ICP27 may allow for prolonged gene expression, cell survival is impaired, in part, due to the abrupt inhibition of cellular DNA synthesis.

d95 also exemplifies a preferred embodiment of the present invention: a ICP4$^{(-)}$ICP27$^{(-)}$ICP22$^{(-)}$ defective HSV triple mutant which is isolated and propagated in a ICP4ICP27 complementing cell line wherein this triple mutant is capable of housing and expressing one or more transgenic sequences such that infection of a host target cell in a gene therapy application will exhibit minimal effect on target cell protein synthesis for up to at least three days post-infection. A ICP4$^{(-)}$ICP27$^{(-)}$ICP22$^{(-)}$ defective HSV triple mutant, as exemplified by d95, exhibits the characteristics of a useful short-term gene therapy vehicle. An example of such a short term application would be direct injection of a d95-based vector directly into a tumor site to express immunotherapeutic transgenes.

d95 can be engineered to express genes that encode cytokines to stimulate immune recognition of the tumor cells, and/or suicide genes for prodrug activation such as, the tk or cytosine deaminase. Thus, the infected tumor cells will be growth arrested but express the therapeutic gene for the potential elimination of the tumor cells that did not get infected. The combination of this approach along with the exploitation of the d95 phenotype is novel.

As noted above for d97, the identification of d95 exemplifies but in no way limits this portion of the invention. It will be within the purview of the artisan to construct a ICP4$^{(-)}$ICP27$^{(-)}$ICP22$^{(-)}$ defective HSV triple mutant by other related methodology. For instance, mutant HSV viral strains d92 and DMP were used in construction of d95. However, it will be appreciated that the present invention encompasses use of any ICP4$^{(-)}$, ICP27$^{(-)}$, ICP22$^{(-)}$, or double mutant strain such as an ICP4$^{(-)}$ICP27$^{(-)}$, ICP22$^{(-)}$ICP4$^{(-)}$, or ICP22$^{(-)}$ICP27$^{(-)}$ strain to generate a ICP4$^{(-)}$ICP27$^{(-)}$ICP22$^{(-)}$ virus. Regardless of the related strategy, the end result will be a HSV mutant strain deleted for ICP4, ICP27 and ICP22, and hence, a HSV mutant strain which again is an excellent candidate for further use as a human gene therapy vector.

The generation of a ICP4$^{(-)}$, ICP0$^{(-)}$, ICP27$^{(-)}$, ICP22$^{(-)}$ virus is accomplished by co-infection of FO6 cells with d97 and d95. During this infection the genomes will recombine. The average recombinational distance to generate the desired ICP4$^{(-)}$, ICP0$^{(-)}$, ICP27$^{(-)}$, ICP22$^{(-)}$ virus by this procedure is 14 kb. This should produce the desired recombinant of a frequency of about 10%. The progeny of this co-infection will be plated on FO6 cells. Small blue plaques, characteristic of the ICP0$^{(-)}$ genotype will be isolated, amplified and screened by Southern blot hybridization for incorporation of the ICP22 allele. Both starting viruses are ICP4$^{(-)}$ and ICP27$^{(-)}$ so the loss of these genes need not be determined. The ICP22$^{(-)}$ progeny will then be checked again for the presence of both Oβ alleles at the ICP0 loci. The resulting ICP4$^{(-)}$, ICP27$^{(-)}$, ICP0$^{(-)}$, ICP22$^{(-)}$ virus will be amplified in FO6 cells.

An additional recombinant HSV mutant strain and additional embodiment of the present invention is a HSV recombinant strain d33 Δ(ICP4:ICP27:UL41) wherein the HSV UL41 gene is mutated in the d92 background. The wild type UL41 gene encodes a 58 kD viral tegument protein involved in the virion-host shutoff (vhs) of protein synthesis. UL41 is a late HSV gene product released during host cell infection. Infection of a eukaryotic cell by wild type HSV is accompanied by early inhibition of host cell metabolism, including DNA and protein synthesis. This viral induced shut-off of host metabolism is linked to destabilization and degradation of host mRNA. Therefore, an ICP4$^{(-)}$ICP27$^{(-)}$ HSV strain further deficient in UL41 confers additional protection against potential cytotoxic effects by severely reducing viral protein synthesis through the knockout of ICP4 and ICP27 as well as inhibiting viral induced shutoff of host cell metabolism. d33 has been generated by a recombinational cross of d92 with a UL41 deficient-HSV strain in the complementing cell line, 26 cells. This HSV triple mutant strain, d33 Δ(ICP4:ICP27:UL41), is comprised of a genome 11 kb shorter than wild type HSV.

Another additional recombinant HSV mutant strain and additional embodiment of the present invention wherein the HSV strain is deficient for ICP4, ICP27, UL41 and the non-essential HSV gene, UL39. In a specific embodiment, presented to exemplify but not limit the claimed invention, d33 was utilized as a template to generate a quadruple HSV mutant deficient in UL39, as well as the ICP4, ICP27 and UL41 mutations within the d33 background. The HSV gene UL39 encodes the large subunit of ribonucleotide reductase, a key enzyme in the pathway reducing ribonucleotides to the corresponding deoxribonucleotides.

The quadruple HSV mutant strain generated from the d92/d33 mutant HSV series is exemplified in the present invention by d94 Δ(ICP4:ICP27:UL41:UL39):β-gal. The heterologous β-gal gene of d94 is abundantly expressed in infected Vero cells minimally altering cell morphology. Therefore, successful infection of the target cell by d94 results in (1) expression of the gene of interest, (2) an extreme reduction in cytotoxic effects due to viral gene expression, and (3) a persistence of host cell protein synthesis due to inactivation of the UL41 gene product.

Therefore, the present invention discloses HSV mutant strains containing multiple deletions in both essential and non-essential viral genes. These HSV mutant strains, exemplified in this specification by d92, d97, d95, d33 and d94, comprise characteristics amenable to use as gene transfer vehicles, including but not limited to (1) the ability to obtain large quantities of recombinant virus, (2) a significant reduction in wild-type reversion, (3) an ability to accept larger foreign DNA fragments for gene transfer applications, (4) minimized interference with host cell protein synthesis, and (5) reduced or even minimal host cell cytotoxicity.

It will be understood by the skilled artisan, in view of the numerous examples presented within this specification, that combinations of HSV mutants disclosed may be generated to add or substitute various deletions disclosed within this specification. For example, it will be within the purview of the skilled artisan to generate HSV strains mutated for UL41 or UL41:UL39 in backgrounds other than an ICP4:ICP27 background, including but not limited to an ICP4:ICP27:ICP22 background, an ICP4:ICP27:ICP0 background, and an ICP4:ICP27:ICP22:ICP0 background. The skilled artisan has access to the required complementing cells lines (i.e., such as 26 cells or FO6) to isolate, characterize and propagate the HSV mutant strain of choice.

Therefore, the uses for the HSV mutant vectors of the present invention include, but are not limited to, (1) in vivo delivery of human therapeutic or prophylactic genes of interest to various cell types, including use in various cancer therapies, (2) in vitro delivery of genes of interest to various cell types, human and/or non-human, (3) use to construct vectors for generation of transgenic mice strains, and (4) use to construct vectors to knockout specific genes in mice strains.

6. EXAMPLE: CONSTRUCTION OF 26 CELLS

The plasmid pSV2 neo contains the gene encoding neomycin phosphoryl transferase and confers resistance to G418 to mammalian cells. The plasmid pK1-2 contains the coding sequence and transcriptional regulatory elements for the expression of ICP4 (DeLuca, et al., 1987, Nucleic Acids Res. 15:4491–4511). It contains approximately 400 bp of HSV-1 sequences beyond the 3' end of the mRNA. The plasmid pKHX-BH contains all the coding sequence of HSV necessary to express ICP27 (Bond, et al, 1984, Virology, 132:368–376). pSV2neo (1 microgram), pK1-2 (3 micrograms), and pKHX-BH (3 μg) were cotransfected using the calcium phosphate precipitation method onto 4×10$^6$ ATCC CCL81 Vero cells. Four hours after the application of the precipitate to the cells, they were subjected to a 15% glycerol shock for a period of 2 mins. After the shock, the cells were incubated in DME plus 10% FBS at 37° C. 24 hours later, the cells were trypsinized and replated at one tenth the original density and G418 was applied (1 mg/ml). After four days, the concentration of G418 was lowered to 400 μg/ml. After two weeks, G418 resistant colonies were observed. These were isolated and expanded. Monolayer cultures from individual clones were infected with d120, to determine the functional presence of the ICP4 gene, and 5dl 1.2, to determine the functional presence of the ICP27 gene.

Of the 67 cell lines tested with d120 and 5dl 1.2, 12 allowed the growth of only d120, 4 allowed the growth of only 5dl 1.2 and, 19 of the lines allowed the growth of both. With many of the lines that allowed the growth of both, virus yield experiments were performed to determine the best cell line to use as an efficient host for both mutant viruses. The plaque of d120 and 5dl 1.2 were closest in size to wild-type virus on a cell line designated 26 cells. The yields of d120 and 5dl 1.2 were 810 and 310 PFU/cell, respectively on 26 cells (Samaniego, et al., 1995. J. Virol. 69:5705–5715). A cell line designated 8 cells were also retained because they only allowed the efficient growth of 5 dl 1.2.

7. EXAMPLE: CONSTRUCTION OF d92, AN ICP4 AND ICP27 DELETION MUTANT d120 and 5dl1.2 were used to co-infect 26 cells at an moi of 5 PFU each. 18 hours later the culture was harvested and the progeny were plated out on 26 cells for the isolation of individual plaques. After the plaques developed, they were picked with a pipet into 0.5 ml medium, freeze-thawed three times and plated on 26 cells (ICP4 and ICP27 complementing), E5 cells (ICP4 complementing), 8 cells (ICP 27 complementing), the Vero cells (noncomplementing). 120 plaque isolates were tested. 29 (24%) of the progeny grew only on E5 cells and 26 cells; these are the ICP4 mutant parent. 63 (53%) grew only on 8 cells and 26 cells; these are the ICP27 mutant parent. 18 (15%) grew on all the cell types; these are wild-type virus recombinant generated by the cross over of DNA from d120 and 5dl 1.2. 10 (8.3%) only grew on 26 cells; these are the ICP27$^{(-)}$ICP4$^{(-)}$ double mutant (Samaniego, et al., 1995, J. Virol. 69:5705–5715). These were checked by Southern blot analysis for the presence of the deletion characteristic of both d120 and 5dl 1.2.

It will be appreciated that the present invention discloses novel ICP4$^{(+)}$ICP27$^{(+)}$ cell lines; a method of producing ICP4$^{(+)}$ICP27$^{(+)}$ cell lines; novel ICP27$^{(-)}$ICP4$^{(-)}$ HSV strains, their generation, and use as vectors; ICP27$^{(-)}$ICP4$^{(-)}$ additional HSV gene(s)$^-$ HSV strains, their generation, and use as vectors; novel vectors comprising the novel HSV strains disclosed herein whose genome contains at least one exogenous gene and an appropriate promoter sequence; methods of using the novel HSV strains disclosed herein as vectors; and methods of using the novel HSV disclosed herein to direct homologous recombination with cellular DNA.

8. EXAMPLE: CONSTRUCTION AND CHARACTERISTICS OF d95 (ICP4$^{(-)}$ICP27$^{(-)}$ ICP22$^{(-)}$)

An ICP4, ICP27, ICP22 (d95) deficient virus was generated by co-infecting E26 cells with d92 (Example Section 7) and DMP. DMP is defective for ICP27 and ICP22, by virtue of the 5dl 1.2 and n199 (McCarthy, et al., 1989, J. Virol. 63:1827; Rice, et al., 1995. J. Virol. 69:5550–5559) alleles, respectively. As disclosed in Example Section 7, d92 is defective for ICP4 and ICP27 by virtue of the d120 and 5dl1.2 alleles, respectively. Therefore, both viruses used in this cross contain the 5dl1.2 allele, ensuring that the progeny would also contain this allele. The progeny from the co-infection were plaqued on E26 cells. Individual plaques were isolated and screened for the ability to grow on E26, and not on E8 cells, which supply ICP27. This was performed to restrict the further analysis of progeny to isolates that were genetically deficient in ICP4. Isolates that only grew on E26 cells were then screened for the incorporation of the n199 allele by Southern blot hybridization. n199 is marked by a HpaI site, which is part of a linker that specifies the stop codon conferring the ICP22 phenotype.

FIG. 5 shows the genome of HSV from nucleotide 120 to the S terminus in the parental orientation, the locations of the genes for ICP4 and ICP22, the structures of DMP, d92, and d95 relative to the relevant HpaI restriction sites (vertical arrows). Also shown are the expected sizes of the ICP4 spanning HpaI fragments and Is joint fragment. A Southern blot of the HpaI restriction digest of d92, DMP and d95, probed with the BamHI Y fragment demonstrated the incorporation of the n199 insertion into the d92 background. The sizes of the shortened fragments in the digest of d95 relative to d92 is consistent with the incorporation of the n199 allele into d95. The sizes of the shortened fragments in the digest of d95 relative to DMP is consistent with the incorporation of both of the 4.1 kb deletions of the ICP4 coding sequence in d92 into d95. Therefore, the HpaI pattern of this region of d95 is consistent with mutations in both ICP4 genes and ICP22. The plaquing behavior of d95 on E26, E5, and E8 cells is consistent with mutations in both copies of the ICP4 gene and ICP27.

In order to visualize the IE proteins synthesized in the mutant infected cells and verify the lack of ICP4, ICP27 and ICP22 synthesis, cycloheximide-treated Vero cell monolayers were infected with the indicated viruses at an m.o.i of 10 PFU/cell and incubated in the presence of cycloheximide for 6 h. The cycloheximide was removed by washing the monolayer, and incubation was continued in the presence of actinomycin D and $^{35}$S-methionine. Under these conditions only the IE proteins are labeled. ICP4, ICP0, ICP27, and ICP22 were visible in the profiles of KOS infected cells. However, the individual mutants were missing the bands corresponding to the intended mutations in the IE genes. More specifically, the data demonstrated that d95 does not synthesize ICP4, ICP27 or ICP22.

To further demonstrate that d95 does not synthesize either ICP4, ICP27, or ICP22, cells infected with d120, d92, and d95 and were metabolically labeled with $^{32}$P-orthophosphate. Extracts from the these infected cells were analyzed by SDS PAGE. A $^{32}$P-orthophosphate-based autoradiogram showed that ICP27 (in d120-infected cells) and ICP22 (in d120- and d92-infected cells) are readily labeled with $^{32}$P. The band corresponding to ICP27 is missing in profiles from d95- and d92-infected cells, while ICP22 was missing in the d95-infected cell profile. The lack of ICP22 in d95 was also evident in a $^{35}$S-methionine profile. These data demonstrate that ICP4 is not expressed in any host cell infected with d120, d92 or d95.

The effect of prolonged viral and cellular gene expression in d95-Vero infected cells was compared to viral and cellular gene expression patterns from d120- and d92-Vero infected cells. First, d95-Vero infected cells retained a morphology more closely resembling, but not identical, to uninfected cells.

The d95 monolayer was intact at 2 days post infection. In contrast, infection of host cells with d120 or d92 at an m.o.i of 10 PFU/cell were amenable to analysis up to 1 day postinfection and these cell monolayers dispersed by 2 days post infection. Fewer d95-infected than uninfected cells remain at day 2 post infection and many of the d95-infected cells consisted of 2 nuclei in one cytoplasmic boundary. The same general effects on toxicity and cell number were observed on HEL cells, although it was difficult to observe multinucleated cells at this level of resolution.

A $^{35}$S-methionine profile provided additional evidence regarding the viral expression patterns of d92- and d95-infected cells. These d92- and d95-infected (m.o.i.=10) Vero cells were labeled with $^{35}$S-methionine at the indicated time post infection and subjected to SDS PAGE analysis. Several observations regarding comparative viral expression patterns between d92-infected cells and d95-infected cells are evident from the data generated. First, the ICP22 band is clearly evident at time 6 h, 12 h, and 24 h in d92-infected cells.

However, ICP22 is not expressed in d95-infected cells. Second, insufficient amounts of protein are detected at 2 and 3 days post infection in d92-infected cells. This is consistent with the results described above and is not conducive to further comparison of viral gene expression in d92-infected cells versus d95-infected cells. d120- and d96-infected (d120 and n199 alleles [ICP4$^{(-)}$ICP22$^{(-)}$] behaved similarly to d92-infected Vero cells with respect to the longevity of protein synthesis. Third, cellular protein synthesis in d95- infected cells remains high up to 3 days infection as compare with mock infected expression. Fourth, ICP0 and ICP6 are abundantly expressed in d95-infected cells at 3 days post infection.

The abundance of several RNA species was measured by Northern blot analysis to further assess gene expression in d95-infected cells. Levels of ICP0, tk and cellular β-tubulin RNA in, d120-infected Vero cells, d92-infected Vero cells, d95-infected Vero cells, and uninfected cells at 6 h and 24 h post infection were thus measured. The analysis was extended to 72 h post infection. ICP0 is abundantly transcribed in the absence of ICP4 but tk is not. The levels of tk in absence of ICP4 are approximately 2–4% of tk levels in the presence of ICP4 (Imbalzano, et al., 1991, J. Virol. 65:565–574). ICP0 RNA was slightly increased in size in d92-infected cells relative to d120-infected cells. The abundance of tk RNA was reduced in d92-infected cells relative to d120-infected cells at 6 h post infection (Samaniego, et al., 1995. J. Virol. 69:5705–5715). Deletion of ICP22 from the d92 background suppressed these effects. The effect on ICP0 is less evident at 24 h post infection and that on tk is no longer observed. Consistent with the labelling of cellular proteins in the SDS PAGE profile, the abundance of β-tubulin RNA was greatest in the d95-infected cells, and is comparable to uninfected cells. Therefore, despite the equal loading of total cellular RNA as determined spectrophotometrically and by the ethidium bromide staining patterns of the ribosomal RNA, the abundance of β-tubulin RNA in d120- and d92-infected cells was rescued relative to d95. This implies that the stability or the transcription of these messages is reduced as a consequence of the genes expressed in d120 and d92, and that the further removal of ICP22 relieved this effect. The data also show that the abundance of all three of the messages in d95-infected cells remained relatively unchanged up to three days post infection. The same patterns of expression of ICP0, tk, and β-tubulin RNA were also seen in HEL cells.

Figure 6A:
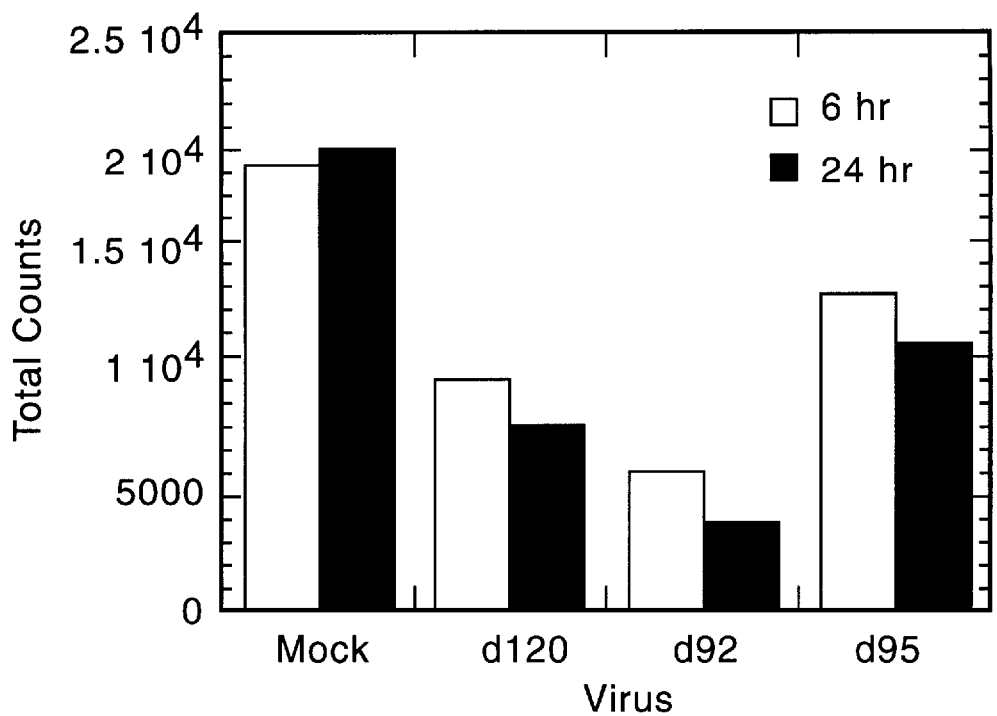
Figure 6B:
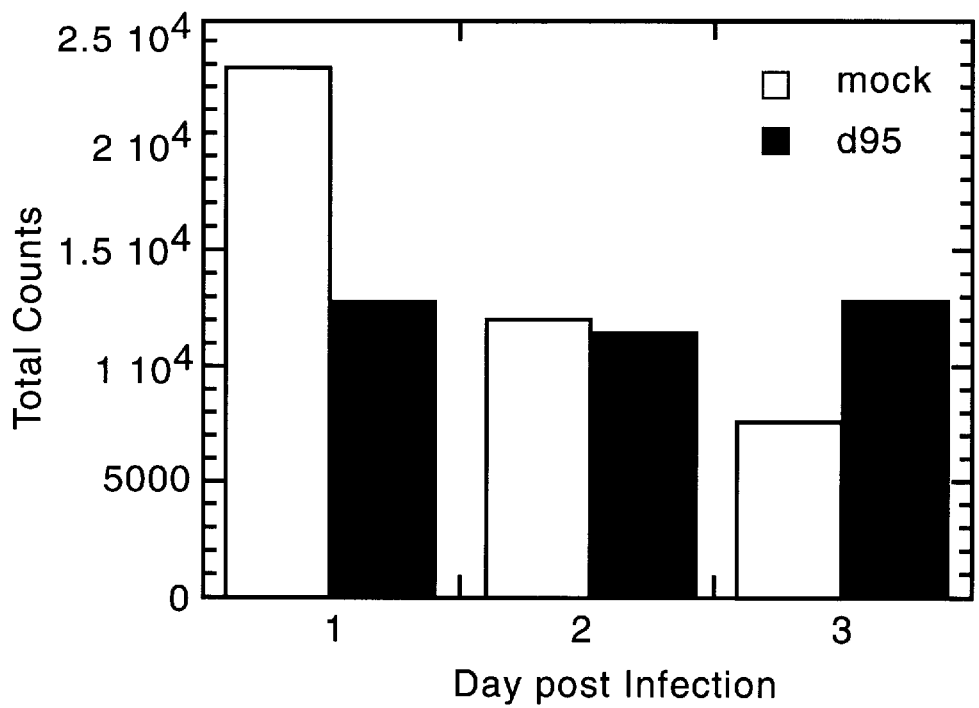

Quantitative analysis of the β-tubulin RNA detected by Northern analysis described above is shown in FIGS. 6A–6C is shown in FIG. 11. At 6 h and 24 h post infection, the level of β-tubulin RNA was reduced in d120-, d92-, and d95-infected cells, with the lowest reduction seen in d95-infected cells (FIG. 6A). β-tubulin RNA levels in d95-infected cells remained constant for 3 days while β-tubulin RNA declined in uninfected cells over the same period (FIG. 6B). This is also the case for the levels of ICP0 and tk RNA over this time interval (FIG. 6B). The simplest interpretation of this data is that HSV proteins expressed from the d95 genome, including ICP0, allow for transcription to continue at a constant rate for three days.

Figure 6C:
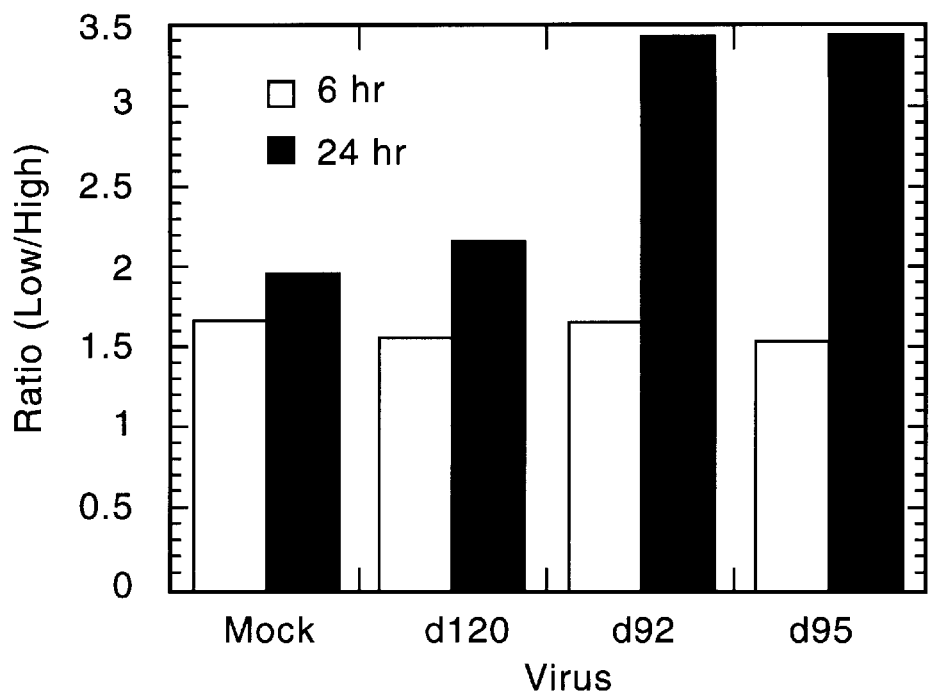
Figure 6D:
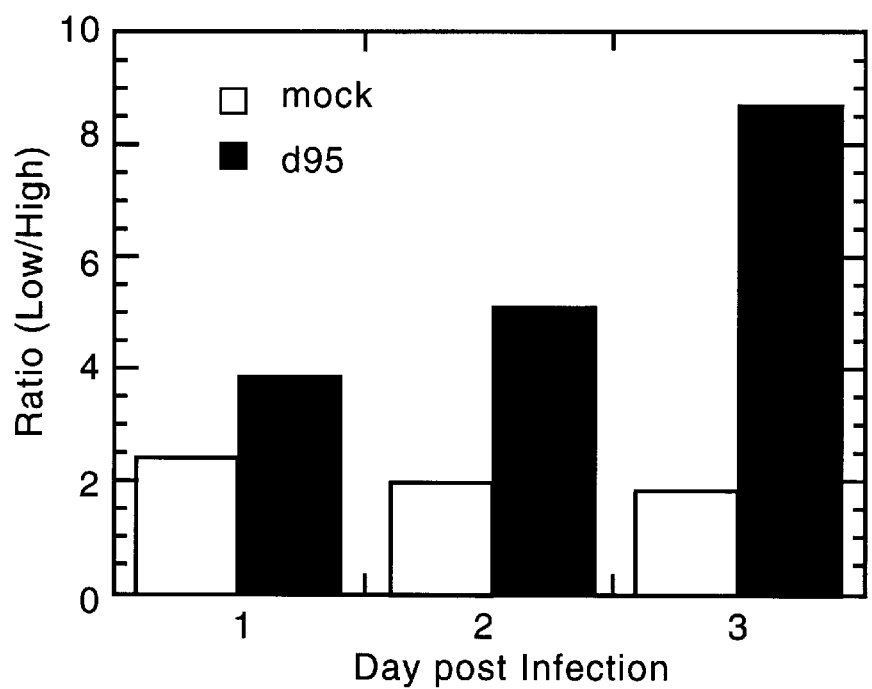

It is clear the data described above that β-tubulin RNA is present in two species. This occurrence is known in the art and is caused by utilization of alternative polyadenylation (poly A$^+$) signals. FIGS. 6C and 6D show the ratio of the low molecular weight (1.8 kb) to high molecular weight (2.6 kb) species, indicative of the relative usage of the proximal and distal poly A$^+$ sites.

This changed as a function of virus at 1 day post infection. Utilization of the proximal signal increased when ICP27 was deleted as demonstrated by the increase in the low/high ratio in d92- and d95-infected cells, relative to d120 and mock infected cells at 24 h post infection (FIG. 6C). The usage of the proximal poly A$^+$ site became more pronounced 2 and 3 days post infection in d95-infected cells relative to uninfected cells (FIG. 6D). Therefore, expression of HSV proteins from the d95 genome, including ICP0, results in the alteration of 3' processing relative to uninfected cells in case the of β-tubulin RNA. Apparently, the additional expression of ICP27 results in the alteration of poly A$^+$ site usage back to a proportion observed in uninfected cells.

d95-infected Vero cells are inhibited in cellular DNA replication and cell division. While cells infected with d95 do not demonstrate the rapid rounding up and detachment from the monolayer, and continue to express genes on the viral genome for three days, they do not increase in number (FIG. 7A). Vero cells in an uninfected monolayer increased in number for two days. In contrast, d95 infected cells did not, and there was a marginal decrease in the number of cells, suggesting that the growth potential of d95-infected cells was inhibited.

To assess the growth potential of d95 infected cells, two experiments were performed. The first involved infecting monolayers of Vero cells with d120, d92 and d95 at different multiplicities, followed by trypsinzing the cells and plating them out for colony forming units (FIG. 7B). The second involves measuring the uptake of $^3$H-thymidine into infected cells (FIG. 7C and FIG. 7D). Using the colony forming assay, d92 inhibited cell viability less than d120. d95 was only marginally less inhibitory than d92, despite the dramatically different appearance of d92- and d95-infected cells described above. FIG. 7B also shows the probability of the cells not being infected following inoculation at a given m.o.i. The survival curves indicate that up to an m.o.i of 3, a single PFU is very efficient in inhibiting colony formation. At an m.o.i. of 10, survival is greater than would be expected from the pattern seen at the lower multiplicities. This indicates that the inhibitory effects may be saturable or that there are are subpopulations of cells that are less susceptible to the inhibitory effects. In summary, all of these viruses had an inhibitory effect on colony forming ability.

It was also determined whether cellular DNA synthesis was inhibited in d95-infected cells. Accordingly, Vero and HEL cells were infected with d95 at an m.o.i. of 10 PFU/cell. At 1, 2, 3, and 4 days post infection, d95-infected and uninfected cells were labelled for 3 hours with $^3$H-thymidine. Following the labelling period, DNA from the cells was isolated and the amount of $^3$H incorporated per microgram of DNA was determined. As is evident in FIGS. 7C and 7D, d95 infection significantly inhibited cellular DNA replication in both Vero and HEL cells, respectively. The drop in uninfected cell labelling at 3 and 4 days post infection is consistent with results of FIG. 7A, probably reflecting contact inhibition.

The other viruses listed in this Example Section could only be analyzed at 1 day post infection. These gave similar results to those obtained for d95 at one day post infection. Therefore, in the absence of ICP4, ICP27, and ICP22, HSV infection results in the loss of cell viability, in part, through the inhibition of DNA synthesis.

The virus d95 abundantly expresses ICP0. Indirect immunofluorescence studies indicate that ICP0 accumulates in the nucleus in large spherical inclusion bodies that can be seen by light microscopy at 2 days post-infection. This data supports the suggestion that such a great accumulation of ICP0, while possibly beneficial for transgene expression, will be deleterious to prolonged host cell survival.

9. EXAMPLE: CONSTRUCTION AND CHARACTERISTICS OF HSV STRAIN d97 (ICP4$^{(-)}$:ICP27$^{(-)}$:ICP0$^{(-)}$):β-gal AND CELL LINE FO6 (ICP4:ICP27:ICP0)

In light of the effect of ICP0 on host cell toxicity, as documented in this Example Section as well as Example Section 8, the present invention also relates to an ICP4, ICP27, ICP0 deficient virus and an ICP4ICP27ICP0 complementing cell line.

In contrast to other exemplified HSV mutant strains disclosed throughout this specification, attempts to delete ICP0 from the d92 background by co-infecting the 26 cells cell line with virus deleted for ICP0 were unsuccessful. The growth dampening effect of deleting ICP0 in a ICP4$^{(-)}$ICP27$^{(-)}$ mutant was unexpectedly greater than that observed for a wild-type background. This would not be expected from the literature which indicates that ICP0$^{(-)}$ viruses can grow in the absence of complementation. Presumably, failed efforts to use E26 cells to isolate ICP4$^{(31)}$ICP27$^{(-)}$ICP0$^{(-)}$ viruses were due to the fact that ICP0$^{(-)}$ yields in the absence of complementation are reduced 100 fold relative to wild-type. By comparison, inactivating UL41, UL39 and ICP22 only reduces viral yields by 3–10 fold. The 100 fold reduction in addition to the less than wild-type complementation of ICP4 and ICP27 in E26 cells makes the isolation of and propagation of ICP4$^{(-)}$, ICP27$^{(-)}$, ICP0$^{(-)}$ virus more difficult.

Therefore, the initial step in generating an HSV virus deficient in ICP4, ICP27 and ICP0 required construction of a ICP4ICP27ICP0 complementing cell line. To this end, the 26 cells cell line, resistant to G418, was transformed with plasmids pW3-HS8 (Sacks and Schaffer, 1987, J. Virol. 61:829–839; 5 µg) and pSV2hyg (which encodes resistance to hygromycin; 1 µg). Colonies were selected in the presence of G418 (400 µg/ml) and hygromycin (300 µg/ml), essentially as described in Example Section 6. All cell lines complemented d92. Only one of the 80 colonies screened also efficiently complemented both d92 and n212, a previously published ICP0 mutant. This clone, FO6, resulted in a 30 fold increase in the number of ICP0 mutant virus plaques. The FO6 cell line was used for the isolation of a HSV virus deficient in ICP4, ICP27 and ICP0.

FO6 cells are somewhat growth impaired because unlike E26 cells, they express low levels of the genes inserted into the cells for purposes of complementation. These are ICP4, ICP27 and ICP0. The growth impairment is presumably due to the toxic effects of these genes. It was also observed that the FO6 cell line would loose the ability to complement ICP0 mutants after approximately 10 passages if both G418 (400 µg/ml) and hygromycin (300 µg/ml) were not included in the growth maintenance medium. Therefore, both of these antibiotics are routinely included in the growth medium. This results in the prolonged ability (approximately 20 passes) of FO6 cells to complement ICP0 mutants. G418 and hygromycin are not added when mutant viruses are grown or plaqued on FO6 cells.

The following scheme was used to inactivate the ICP0 gene in the d92 genome. Initially the virus Oβ was constructed in the following manner. The plasmid pW3-HS8 contains a 4.5 kb SacI to PstI insert which encodes the ICP0 gene. The initiator methionine codon for ICP0 is present in an unique NcoI site (CCATGG) in pW3-HS8. 700 bp into the protein coding sequence from NcoI is an unique BamHI site. The sequence contained in the 700 bp Nco1-BamHI fragment was replaced with the BamHI fragment from the plasmid pSC8 that encodes the *E. coli* β-galactosidase gene. This was done after deleting the 700 bp NcoI-Bam HI fragment and modifying the NcoI site in the ICP0 plasmid with synthetic linkers such that it accepts the β-gal-encoding BamHI fragment and puts the ATG in frame with the β-gal protein. This construction puts β-gal under ICP0 control. The resulting plasmid is linearized and cotransfected with wild type virus DNA onto Vero cells. Recombinant plaques were identified by staining with X-Gal. The insertion of β-gal into both ICP0 loci was confirmed by Southern blot analysis.

The virus Oβ, which contains a deletion of the ICP0 genes, and an insertion of β-galactosidase under the transcriptional control of the ICP0 promoter was co-infected with d92 on FO6 cells. Blue plaques were screened for the presence of the ICP4, ICP27 and ICP0 alleles by plaque assay on different cell lines and by restriction fragment blot analysis. From this the virus d97 was isolated.

KOS, and the 5dl1.2, d120, d92, d95, d96, and d97 HSV mutant strains were inoculated onto Vero cells, first in the presence of cycloheximide for 6 h to allow IE transcripts to accumulate followed by removal of the cycloheximide and addition of actinomycin D plus $^{35}$S-methionine for 3 h to label translated IE proteins. The data discussed above demonstrated that (1) ICP4 was not expressed in d120, d92, d95 and d97; (2) ICP27 was not expressed in 5dl1.2, d92, d95 and d97; (3) ICP0 was not expressed in d97 and d96; (4) ICP22 was not expressed in d95; and (5) β-gal was expressed in d97.

$^{35}$S-methionine labeled proteins at 6–9 h post infection in the absence of metabolic inhibitors were compared. The d97 protein synthesis pattern is similar in the absence and presence of cycloheximide. In other words, the protein synthesis in d97 infected cells was similar to that seen in the absence of de novo protein synthesis, implying that the virus might have a minimal effect on host cell metabolism, and hence cytotoxicity.

To assess toxicity, d97 was compared to d92 and d95 in colony survival tests. Vero cells were infected with the viruses at mois of 1, 3, and 10. At 6 h post infection the cells were trypsinized and plated for surviving colonies. FIG. 8 shows that survival was substantially increased by the deletion of ICP0. These data, along with the data from Example Section 8, demonstrate that ICP0 is a major determinate of vector toxicity. To further assess this, Vero cells were infected with d97 at an moi of 3 PFU/cell and 3 and 14 days later stained for β-gal. All the cells are intact and most are expressing β-gal at 3 days. At 14 days this number decreases but still remains higher than that previously observed for other herpes virus vectors. When L7 cells, which express ICP0, are similarly infected, β-gal expression is even greater, however the monolayer is destroyed. This further demonstrates that ICP0 is a major determinant of vector toxicity, and that a ICP4$^{(-)}$:ICP27$^{(-)}$:ICP0$^{(-)}$ mutant such as d97 will be useful as a gene delivery vector. d97 was also used to infect human embryonic lung cells, and β-gal expression was determined by X-gal staining over a 16 day period. A comparison of uninfected and d97-infected cells stained with X-gal at 2, 4, 8, and 16 days post-infection indicated that β-gal activity could again easily be detected at 16 days post-infection with no observable effects on host cell morphology.

To quantify the extent of expression, Vero cells infected with d97 as described above were harvested over the course of 2 weeks and assayed for β-gal activity. Activity peaked at 1 day post infection, and dropped to about 5 percent of this level at 14 days post infection (FIG. 9). In conclusion, expression from an HSV IE promoter, such as the ICP0 promoter, in d97 is abundant at early times post infection (FIG. 9), resulting in a strong band on SDS gel electrophoresis. This is due to activation by VP16 in the virion particle. VP16 turns over with time, and in the absence of ICP0 to further induce IE promoters, IE gene expression drops to 5% of the maximum levels at 2 weeks post infection. Despite this reduction, expression remains substantial over time and may be sufficient for a variety of applications. Furthermore, the inclusion of heterologous systems for regulating gene expression in viruses such as d97 may provide even further utility to the present invention as disclosed, exemplified and claimed.

10. EXAMPLE: CONSTRUCTION OF d33 Δ (ICP4:ICP27:UL41)

ΔSma contains an internal deletion within the UL41 coding region that results in expression of a truncated protein which is not incorporated into virions (Read, et al., 1993, J. Virol. 67:7149–7160). The progeny from a recombinational cross between d92 and ΔSma were plated on 26 cells and plaques were chosen for Southern blot analysis. Isolates were selected on the basis of having deletions in ICP4, ICP27 and UL41. d33 is one such isolate.

A long continuous protein labeling pattern for uninfected Vero cells, wild type HSV (KOS), d120 (ICP4$^{(-)}$), 5dl 1.2 (ICP27$^{(-)}$), ΔSma (UL41$^{(-)}$), and d33 Δ(ICP4:ICP27:UL41), d92 Δ(ICP4:ICP27) was prepared. All viruses except ΔSma and d33 show some degree of shut off of host cell protein synthesis. This can be attributed to the lack of a stable vhs activity from these UL41$^{(-)}$ strains. Late genes are not expressed in 5dl 1.2 infected cells and only ICP0, ICP6 and ICP27 are expressed in d120 infected cells. Viral gene expression is severely impaired in the d92 background. The only discernable viral proteins present in the d92 profile are ICP6 and ICP0.

The data further demonstrate that UL41 is mutated in the d92 background (i.e., d33), the observed protein expression profile is similar to that seen in uninfected cells. Despite the dramatic restriction of viral gene expression observed for d33 and d92 in noncomplementing cells, wild-type levels of viral gene expression are observed in the complementing cell line, 26 cells. These viruses can be obtained in quantities discussed within this specification (i.e., titers in excess of $10^9$ PFU/ml). Therefore, this specification discloses the generation of large quantities of these mutant HSV vectors that do not have any wild-type recombinants, and upon infection of cells, the pattern of protein synthesis resembles that seen in uninfected cells.

11. EXAMPLE: CONSTRUCTION OF d94 Δ (ICP$^4$:ICP27:UL41:UL39):β-GAL

The plasmid pKXGβ3 was previously used to construct a ΔICP6 recombinant mutant which expresses β-Gal (Goldstein and Weller, 1988, J. Virol. 62:196–205). d33 was cotransfected with pKXGβ3 and the resulting progeny were plated on 26 cells and stained with X-gal. Blue plaques were isolated, analyzed and amplified. The resulting HSV recombinant mutant was d94 Δ(ICP4:ICP27:UL41:UL39):β-gal. All procedures were carried out as described throughout these Example Sections.

Wild-type levels of d94 viral gene expression are observed in 26 cells despite a restriction of d94 viral gene expression in Vero cells. This result correlates with the data obtained for the expression profile of d92 and d33 in Vero and 26 cells, as discussed in the previous Example Section.

The d94 phenotype was analyzed in noncomplementing cells. An X-Gal stain of Vero cells infected at an m.o.i. of 0.3 PFU d94/cell showed abundant LacZ at two and three days post infection. The lac-Z marker of d94 is abundantly expressed and Vero cell morphology is apparently unchanged relative to uninfected cells. Therefore, d94 represents an example of a less toxic HSV recombinant vector that expresses the gene of interest subsequent to target host cell infection.

Recombinant HSV vectors of the present invention show marked reduction in cytotoxicity in comparison with ICP4$^{(-)}$ mutants such as d120, which are currently being used as vectors. Cytotoxic effects are reduced by decreasing the number and type of HSV genes which are expressed subsequent to infection of the host cell, as well as inhibiting post-infection vhs functions. The survival of Vero cells as a function of m.o.i. are shown in FIG. 10. Monolayers of Vero cells were infected with d94 at the m.o.i.s listed in FIG. 10, incubated for 6 hours and then trypsinized, diluted, and plated out for colonies.

12. DEPOSIT OF MICROORGANISMS

The following ICP4ICP27 complementing cell line and HSV-1 ICP4$^{(-)}$ICP27$^{(-)}$ mutant strain were deposited with the American Type Culture Collection (ATCC), 12301 Parklawn Drive, Rockville, Md. 20852, on Apr. 21, 1993, and were converted to deposits under the terms of the Budapest Treaty on Mar. 7, 1996, having been assigned accession numbers as follows:

|  | Accession No. |
| --- | --- |
| Cell line "26 cells" | CRL 11332 |
| HSV-1 strain "d92" | VR 2406 |

The following ICP4ICP27ICP0 complementing cell line was deposited with the American Type Culture Collection (ATCC), 12301 Parklawn Drive, Rockville, Md. 20852, on Jan. 30, 1996 under the terms of the Budapest Treaty and assigned the following accession number:

|  | Accession No. |
| --- | --- |
| Cell line "F06" | CRL 12028 |

The following HSV-1 ICP4$^{(-)}$ICP27$^{(-)}$ additional IE genes mutant strains were deposited with the American Type Culture Collection (ATCC), 12301 Parklawn Drive, Rockville, Md. 20852, on Jan. 30, 1996 under the terms of the Budapest Treaty, and assigned accession numbers as follows:

|  | Accession No. |
| --- | --- |
| HSV-1 strain "d95" | VR 2523 |
| HSV-1 strain "d97" | VR 2524 |

Whereas particular embodiments of the invention has been described hereinbefore, for purposes of illustration, it would be evident to those skilled in the art that numerous variations of the details may be made without departing from the invention as defined in the appended claims.

What is claimed is:

1. A cell line which comprises DNA encoding herpes simplex virus (HSV) proteins ICP4, ICP27, and ICP0.

2. The cell line of claim 1 which further comprises DNA encoding antibiotic resistance.

3. The cell line of claim 2 which further comprises DNA encoding neomycin resistance.

4. The cell line of claim 2 which further comprises DNA encoding hygromycin resistance.

5. The cell line of claim 2 which further comprises DNA encoding neomycin resistance and hygromycin resistance.

6. The cell line of claim 2, wherein said cells are Vero cell derivatives.

7. The cell line of claim 3, wherein said cells are Vero cell derivatives.

8. The cell line of claim 4, wherein said cells are Vero cell derivatives.

9. The cell line of claim 5, wherein said cells are Vero cell derivatives.

10. The cell line of claim 9 which is FO6.

11. An HSV strain comprising a genome defective for the HSV ICP4, ICP27, and ICP0 genes.

12. The HSV strain of claim 11 wherein said defects in said ICP4 and ICP27 genes are contributed by d92.

13. The HSV strain of claim 12 which is d97.

14. An HSV vector comprising
   (a) a genome defective for the HSV ICP4, ICP27, and ICP0 genes, and
   (b) at least one exogenous gene.

15. The vector of claim 14 wherein said defects in said ICP4, ICP27, and ICP0 genes are contributed by d97.

16. The vector of claim 14 wherein said genome is further defective for at least one additional HSV gene.

17. The vector of claim 15, wherein said genome is further defective for at least one additional HSV gene.

18. The vector of claim 16, wherein said additional HSV gene is ICP22.

19. The vector of claim 16, wherein said additional HSV genes are ICP22 and ICP6.

20. The method of claim 16 wherein said additional HSV gene is UL41.

21. The vector of claim 17, wherein said additional HSV gene is ICP22.

22. The vector of claim 17, wherein said additional HSV genes are ICP22 and ICP6.

23. The method of claim 17 wherein said additional HSV gene is UL41.

24. A method of producing a mutant HSV which comprises:
   infecting an ICP4$^{(+)}$/ICP27$^{(+)}$/ICP0$^{(+)}$ cell line expressing complementing levels of ICP4, ICP27, and ICP0 with a mutant HSV;
   incubating said cell line in a tissue culture medium; and,
   collecting said mutant HSV produced by said cell line.

25. The method of claim 24 wherein said cell line is FO6.

26. The method of claim 24 wherein said mutant HSV comprises a genome defective for the HSV ICP4, ICP27, and ICP0 genes.

27. The method of claim 24, wherein said mutant HSV comprises a genome defective for the HSV ICP4, ICP27, ICP0 and ICP22 genes.

28. The method of claim 25 wherein said mutant HSV comprises a genome defective for the HSV ICP4, ICP27, and ICP0 genes.

29. The method of claim 25 wherein said mutant HSV comprises a genome defective for the HSV ICP4, ICP27, ICP0 and ICP22 genes.

30. The method of claim 26 wherein said mutant HSV is d97.

31. The method of claim 28 wherein said mutant HSV is d97.

32. A method of expressing an exogenous gene within an isolated mammalian cell which comprises infecting said cell with an HSV vector comprising a genome (a) defective for the HSV ICP4, ICP27, and ICP0 genes, and (b) comprising said exogenous gene, whereby said gene is expressed within said cell.

33. The method of claim 32 wherein said polynucleotide encodes a cytokine.

34. The method of claim 32 wherein said polynucleotide encodes cytosine deaminase.

35. The method of claim 32 wherein said polynucleotide encodes thymidine kinase.

36. The method of claim 32 wherein said HSV vector is further deficient for at least one additional HSV gene.

37. The method of claim 32 wherein said HSV vector comprises a d97 background.

38. The method of claim 36 wherein said additional HSV gene is ICP22.

39. The method of claim 36 wherein said additional HSV gene is ICP6.

40. The method of claim 36 wherein said additional HSV gene is UL41.

41. A method of directing homologous recombination with cellular DNA, said method comprising infecting an isolated cell with an HSV vector, said vector comprising a genome (a) defective for the HSV ICP4 and ICP27 genes and (b) comprising a DNA sequence homologous to said cellular DNA, whereby homologous recombination occurs between said genome and said cellular DNA.

42. The method of claim 41, wherein said genome of said HSV vector is defective for an additional HSV gene.

43. The method of claim 42, wherein said additional gene is ICP0.

44. The method of claim 42, wherein said additional gene is ICP6.

45. The method of claim 42, wherein said additional gene is ICP22.

46. The method of claim 42, wherein said additional HSV gene is UL41.

47. The method of claim 42, wherein said genome of said HSV vector is defective for all immediate early genes.

* * * * *